United States Patent [19]

Schneider

[11] 4,128,713

[45] Dec. 5, 1978

[54] 6,7-DIDEHYDRO-PGI$_1$ COMPOUNDS

[75] Inventor: William P. Schneider, Kalamazoo Township, Kalamazoo County, Mich.

[73] Assignee: The Upjohn Company, Kalamazoo, Mich.

[21] Appl. No.: 860,673

[22] Filed: Dec. 15, 1977

[51] Int. Cl.$^2$ ............................................. C07D 307/93
[52] U.S. Cl. .................................... 542/426; 542/429; 544/131; 544/153; 544/376; 544/364; 260/244.4; 260/326.36; 260/346.22; 260/346.73; 546/269; 546/256; 546/194; 546/196
[58] Field of Search ....................... 260/346.22, 346.73, 260/293.58, 295 K, 295 F, 296 B, 326.36; 542/426, 429; 544/153, 376

[56] References Cited

PUBLICATIONS

Johnson et al., Prostaglandins 12, 915, (1976).

*Primary Examiner*—Henry R. Jiles
*Assistant Examiner*—Bernard Dentz
*Attorney, Agent, or Firm*—Robert A. Armitage

[57] ABSTRACT

This invention relates to certain structural and pharmacological analogs of 5,6-dihydroprostacyclin (PGI$_1$) wherein an endocyclic double bond is present at the C-6 to C-7 position. These novel unsaturated prostacyclin-type compounds are useful for the pharmacological purposes for which prostacyclin is used, e.g., as antithrombotic agents, smooth muscle stimulators, gastric antisecretory agents, antihypertensive agents, antiasthma agents, nasal decongestants, or regulators of fertility and procreation.

51 Claims, No Drawings

6,7-DIDEHYDRO-PGI₁ COMPOUNDS

BACKGROUND OF THE INVENTION

This invention relates to novel structural and pharmacological analogs of prostacyclin (PGI₂) and 5,6-dihydroprostacyclin (PGI₁). In particular, the present invention relates to prostacyclin-type compounds wherein an endocyclic double bond is present at C-6 to C-7.

Prostacyclin is an endogenously produced compound in mammalian species, being structurally and biosynthetically related to the prostaglandins (PG's). In particular, prostacyclin exhibits the following structure and atom numbering:

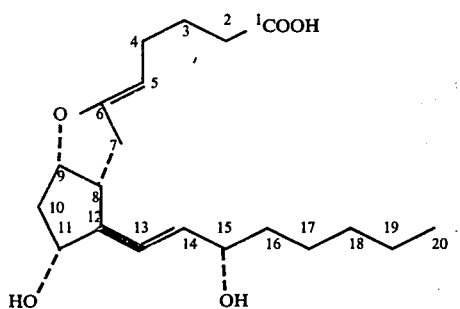

5,6-Dihydroprostacyclin exhibits the following structure and atom numbering:

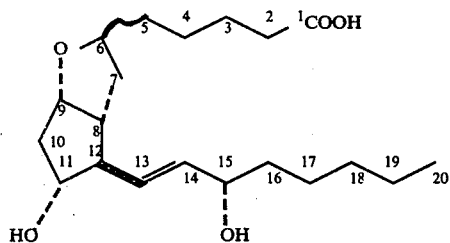

As is apparent from inspection of formulas I and II, prostacyclin and 5,6-dihydroprostacyclin (i.e., PGI₁) bear a structural relationship to PGF₂α, which exhibits the following structure and atom numbering:

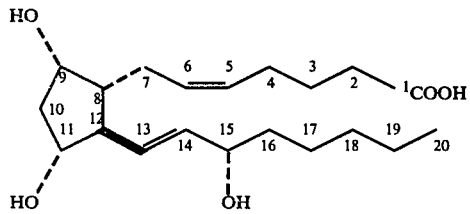

As is apparent by reference to formula III, prostacyclin and 5,6-dihydroprostacyclin may be trivially named as a derivative of PGF-type compounds. Accordingly, prostacyclin is trivially named 9-deoxy-6,9α-epoxy-(5Z)-5,6-didehydro-PGF₁ and 5,6-dihydroprostacyclin is named 9-deoxy-6,9α-epoxy-PGF₁. For description of the geometric stereoisomerism employed above, see Blackwood et al., Journal of the American Chemical Society 90, 509 (1968). Further, for a description of prostacyclin and its structural identification, see Johnson et al., Prostaglandins 12, 915 (1976).

For convenience, the novel prostacyclin analogs described herein will be referred to by the trivial, art-recognized system of nomenclature described by N. A. Nelson, Journal of Medicinal Chemistry, 17, 911 (1974) for the prostaglandins. Accordingly, all of the novel prostacyclin derivatives herein will be named either as 9-deoxy-PGF₁-type compounds or alternatively and preferably as PGI₁ or PGI₂ derivatives.

In formulas I and II above, as well as in formulas hereinafter, broken line attachments to any ring indicate substituents in "alpha" (α) configuration, i.e., below the plane of such ring. Heavy solid line attachments to any ring indicate substituents in "beta" (β) configuration, i.e., above the plane of such ring. The use of wavy lines (~) herein will represent attachment of substituents in either the alpha or beta configuration or attachment in a mixture of alpha and beta configurations.

The side-chain hydroxy at C-15 in the above formulas is in S or R configuration, as determined by the Cahn-Ingold-Prelog sequence rules. See J. Chem. Ed. 41:16 (1964). Also, see Nature 212, 38 (1966) for discussion of the stereochemistry of the prostaglandins, which discussion applies to the novel prostacyclin analogs herein. Expressions such as C-2, C-15, and the like, refer to the carbon atom in the prostaglandin or prostacyclin analog which is in the position corresponding to the position of the same number in PGF₂α or prostacyclin, as enumerated above.

Molecules of prostacyclin and the novel, asymmetric prostacyclin analogs each have several centers of asymmetry, and can exist in racemic (optically inactive) form and in either of the two enantiomeric (optically active) forms, i.e., the dextrorotatory and levorotatory forms. As drawn, the above formula for prostacyclin corresponds to that endogenously produced in mammalian tissues. In particular, refer to the stereoconfiguration at C-8 (alpha), C-9 (alpha), C-11 (alpha), and C-12 (beta) of endogenously-produced prostacyclin. The mirror image of the above formula for prostacyclin represents the other enantiomer. The racemic forms of prostacyclin contains equal numbers of both enantiomeric molecules, and the above formula I and its mirror image is needed to represent correctly the corresponding racemic prostacyclin.

For convenience hereinafter, use of the term prostaglandin ("PG") or prostacyclin ("PGI₂") will mean the optically active form of that prostaglandin or prostacyclin thereby referred to with the same absolute configuration as PGF₂α, obtained from mammalian tissues.

The term "prostaglandin-type" or "prostacyclin-type" (PG-type or PGI-type) product, as used herein, refers to any monocyclic or bicyclic cyclopentane derivative herein which is useful for at least one of the same pharmacological purposes as the prostaglandins or prostacyclin, respectively.

The formulas as drawn herein, which depict a prostaglandin-type or prostacyclin-type product or an intermediate useful in their respective preparations, each represent the particular stereoisomer of the prostaglandin-type or prostacyclin-type product which is of the same relative stereochemical configuration as a corresponding prostaglandin or prostacyclin obtained from mammalian tissues, or the particular stereoisomer of the intermediate which is useful in preparing the above stereoisomer of the prostaglandin-type or prostacyclin-type products.

The term "prostacyclin analog", as used herein, represents that stereoisomer of a prostacyclin-type product which is of the same relative stereochemical configuration as prostacyclin obtained from mammalian tissues or a mixture comprising that stereoisomer and the enantiomer thereof. In particular, where a formula is used to depict a prostacyclin-type product herein, the term "prostacyclin analog" refers to the compound of that formula or a mixture comprising that compound and the enantiomer thereof.

In addition to the above reference disclosing prostacyclin, certain positional isomers thereof have allegedly been discovered by C. Pase-Asiak and L. S. Wolfe. See for example their report in Biochem. 10:3657 (1971), purporting to describe 7,8-didehydro-$PGI_1$ and 8,9-didehydro-$PGI_1$. Further, another positional isomer of prostacyclin, trans-4,5-didehydro-$PGI_1$, has been reported by Nicolaou, et al., J.C.S. Chem. Comm. 1977:331-332 and Corey, et al., J.A.C.S. 99:2006-2008 (1977). These three positional isomers would exhibit respectively the following structural formulas:

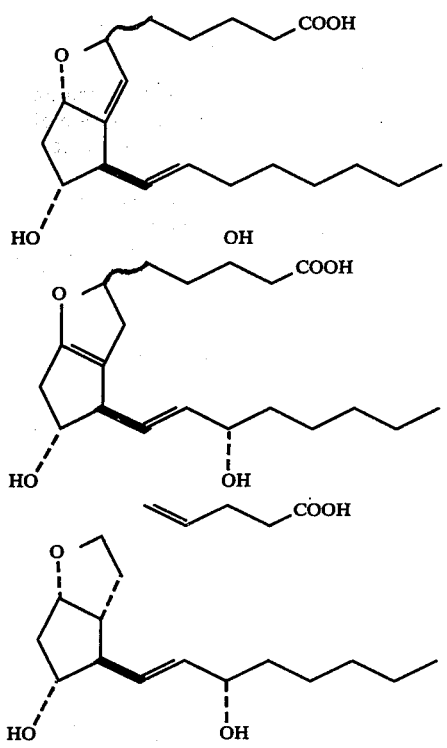

SUMMARY OF THE INVENTION

The present invention particularly comprises:

I. a prostacyclin intermediate of the formula

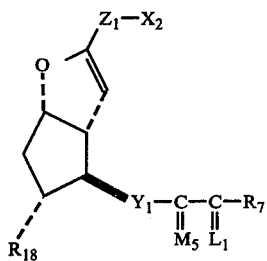

wherein $Z_1$ is (1) —$(CH_2)_g$—$(CH_2)_2$—$CH_2$—, or
(2) —$(CH_2)_g$—$(CH_2)_2$—$CF_2$—, wherein g is the integer one, 2, or 3;

wherein $R_{18}$ is hydrogen; alkanoyloxy of two to 8 carbon atoms, inclusive, or alkanoyloxymethyl of two to 8 carbon atoms, inclusive;

wherein $Y_1$ is (1) trans—CH=CH—,
(2) cis—CH=CH—,
(3) —$CH_2CH_2$—, or
(4) —C≡C—;

wherein $M_5$ is

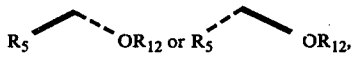

wherein $R_5$ is hydrogen or methyl and $R_{12}$ is alkanoyl of two to 8 carbon atoms, inclusive;

wherein $L_1$ is

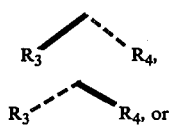

a mixture of

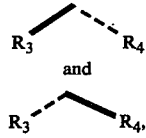

wherein $R_3$ and $R_4$ are hydrogen, methyl, or fluoro, being the same or different, with the proviso that one of $R_3$ and $R_4$ is fluoro only when the other is hydrogen or fluoro;

wherein $X_2$ is (1) —$COOR_2$ wherein $R_2$ is alkyl of one to 12 carbon atoms, inclusive; cycloalkyl of 3 to 10 carbon atoms, inclusive; aralkyl of 7 to 12 carbon atoms, inclusive; phenyl; phenyl substituted with one, two or three chloro or alkyl of one to 3 carbon atoms; phenyl substituted in the para position by

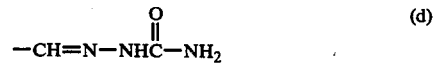

wherein $R_{25}$ is methyl, phenyl, acetamidophenyl, benzamidophenyl, or —$NH_2$; $R_{26}$ is methyl, phenyl, —$NH_2$, or methoxy; and $R_{27}$ is hydrogen or acetamido; phenacyl, i.e.,

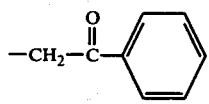

or phenacyl substituted in the para position by chloro, bromo, phenyl, or benzamido;

(2)

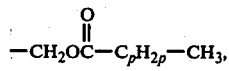

wherein p is zero, one, 2, 3, 4, 5, or 6;

(3) —$CH_2NL_2L_3$ wherein $L_2$ and $L_3$ are hydrogen or alkyl of one to 4 carbon atoms, inclusive; or (4) -$COL_4$, wherein $L_4$ is (a) amino of the formula -$NR_{21}R_{22}$; wherein $R_{21}$ and $R_{22}$ are (i) hydrogen;
(ii) alkyl of one to 12 carbon atoms, inclusive;
(iii) cycloalkyl of 3 to 10 carbon atoms, inclusive;
(iv) aralkyl of 7 to 12 carbon atoms, inclusive;
(v) phenyl;
(vi) phenyl substituted with one, 2, or 3 chloro, alkyl of one to 3 carbon atoms, inclusive, hydroxy, carboxy, alkoxycarbonyl of one to 4 carbon atoms, inclusive, ot nitro;
(vii) carboxyalkyl of one to 4 carbon atoms, inclusive;
(viii) carbamoylalkyl of one to 4 carbon atoms, inclusive,
(ix) cyanoalkyl of one to 4 carbon atoms, inclusive;
(x) acetylalkyl of one to 4 carbon atoms, inclusive;
(xi) benzoylalkyl of one to 4 carbon atoms, inclusive;
(xii) benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro;
(xiii) pyridyl;
(xiv) pyridyl substituted by one, 2, or 3 chloro, alkyl of one to 3 carbon atoms, inclusive, or alkoxy of one to 3 carbon atoms, inclusive;
(xv) pyridylalkyl of one to 4 carbon atoms, inclusive;
(xvi) pyridylalkyl substituted by one, 2, or 3 chloro, alkyl of one to 3 carbon atoms, inclusive, hydroxy, or alkoxy of one to 3 carbon atoms, inclusive;
(xvii) hydroxyalkyl of one to 4 carbon atoms, inclusive;
(xviii) dihydroxyalkyl of one to 4 carbon atoms, or
(xix) trihydroxyalkyl of one to 4 carbon atoms; with the further proviso that not more than one of $R_{21}$ and $R_{22}$ is other than hydrogen or alkyl;

(b) cycloamino selected from the group consisting of

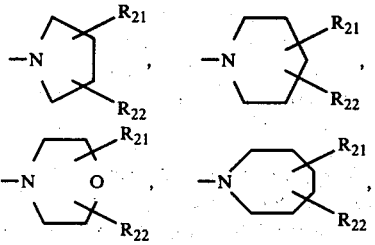

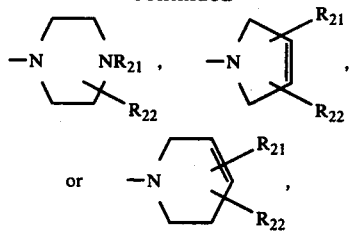

wherein $R_{21}$ and $R_{22}$ are as defined above, (c) carbonylamido of the formula —$NR_{23}COR_{21}$, wherein $R_{23}$ is hydrogen or alkyl of one to 4 carbon atoms and $R_{21}$ is as defined above;

(d) sulphonylamino of the formula —$NR_{23}SO_2R_{21}$, wherein $R_{21}$ and $R_{22}$ are as defined above; or (e) hydrazino of the formula —$NR_{23}R_{24}$, wherein $R_{23}$ is as defined above and $R_{24}$ is amino of the formula —$NR_{21}R_{22}$, as defined above, or cycloamino, as defined above;

wherein $R_7$ is (1) —$(CH_2)_m$—$CH_3$,

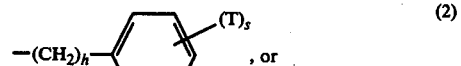

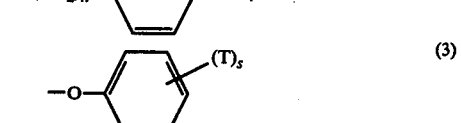

wherein m is the integer one to 5, inclusive, h is the integer zero to 3, inclusive; s is the integer zero, one, 2, or 3, and T is chloro, fluoro, trifluoromethyl, alkyl of one to 3 carbon atoms, inclusive, or alkoxy of one to 3 carbon atoms, inclusive, with the proviso that not more than two T's are other than alkyl; or II. a prostacyclin analog of the formula

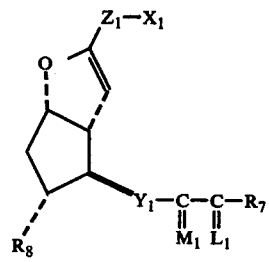

wherein $Y_1$, $Z_1$, $L_1$, and $R_7$ are as defined above; wherein $X_1$ is (1) —$COOR_{10}$ wherein $R_{10}$ is $R_2$, hydrogen, or a pharmacologically acceptable cation;

(2) —$CH_2OH$;

(3) —$CH_2NL_2L_3$ wherein $L_2$ and $L_3$ are as defined above; or (4) —$COL_4$, wherein $L_4$ is as defined above; wherein $M_1$ is

wherein $R_5$ is hydrogen or methyl; and wherein $R_8$ is hydrogen, hydroxy, or hydroxymethyl.

By virtue of the endocyclic unsaturation the novel compounds herein which are prostacyclin analogs or intermediates, as indicated above, are all named as 6,7-didehydro-$PGI_1$-type compounds.

For the novel compounds herein where $Z_1$ is $—(CH_2)_g—(CH_2)_2— CF_2—$, such compounds are referred to herein as 2,2-difluoro-$PGI_1$-type compounds.

When g is 2 or 3, the compounds described herein are additionally named as 2a-homo-$PGI_1$-type or 2a,2b-dihomo-$PGI_1$-type compounds, respectively. In this event the additional methylene or ethylene group is considered for the purposes of nomenclature as though it were inserted between the carbon atoms C-2 and C-3. Further, such additional carbon atoms are denoted as C-2a and C-2b, counting from the C-2 to the C-3 carbon atoms, respectively.

The novel prostacyclin analogs herein wherein $R_8$ is hydrogen or hydroxymethyl are respectively referred to as 11-deoxy-$PGI_1$-type or 11-deoxy-11-hydroxymethyl-$PGI_1$-type compounds. Additionally, when $Y_1$ is cis-CH=CH—, —$CH_2CH_2$—, or —C≡C—, the novel compounds thereby referred to are named as 13-cis-$PGI_1$-type, 13,14-dihydro-$PGI_1$-type, or 13,14-didehydro-$PGI_1$-type compounds.

Novel compounds herein wherein $M_1$ is

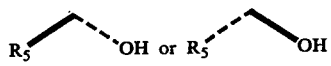

and $R_5$ is methyl are referred to as 15-methyl-$PGI_1$-type compounds.

With the exception of the 13-cis-$PGI_1$-type compounds described above, all the above compounds exhibiting a hydroxy in the beta configuration at C-15 are additionally referred to as 15-epi-$PGI_1$-type compounds. For the 13-cis-$PGI_1$-type compounds herein, only compounds exhibiting the hydroxy in the alpha configuration at C-15 are referred to as 15-epi-$PGI_1$-type compounds. The rationale for this system of nomenclature with respect to the natural and epimeric configurations at C-15 is described in U.S. Pat. No. 4,016,184, issued Apr. 5, 1977.

When $R_7$ is -$(CH_2)_m$-$CH_3$, wherein m is as defined above, the novel compounds herein are named as 19,20-dinor-$PGI_1$-type, 20-nor-$PGI_1$-type, 20-methyl-$PGI_1$-type or 20-ethyl-$PGI_1$-type compounds when m is one, 2, 4, or 5, respectively;

When $R_7$ is

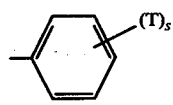

wherein T and s are as defined above, and neither $R_3$ nor $R_4$ is methyl, the novel compounds herein are named as 16-phenyl-17,18,19,20-tetranor-$PGI_1$-type compounds, when s is zero. When s is one, 2, or 3, the corresponding compounds are named as 16-(substituted phenyl)-17,18,19,20-tetranor-$PGI_1$-type compounds. When one and only one of $R_3$ and $R_4$ is methyl or both $R_3$ and $R_4$ are methyl, then the corresponding compounds wherein $R_7$ is as defined in this paragraph are named as 16-phenyl- or 16-(substituted phenyl)-18,19,20-trinor-$PGI_1$-type; or 16-methyl-16-phenyl- or 16-methyl- or 16-(substituted phenyl)-18,19,20-trinor-$PGI_1$-type compounds, respectively.

When $R_7$ is

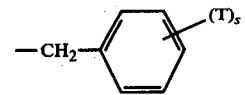

wherein T and s are as defined above, the novel compounds herein are named as 17-phenyl-18,19,20-trinor-$PGI_1$-type compounds, when s is zero. When s is one, 2, or 3, the corresponding compounds are named as 17-(substituted phenyl)-18,19,20-trinor-$PGI_1$-type compounds.

When $R_7$ is

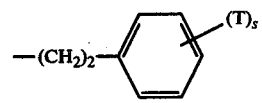

wherein T and s are as defined above, the novel compounds herein are named as 18-phenyl-19,20-dinor-$PGI_1$-type compounds, when s is zero. When s is one, 2, or 3, the corresponding compounds are named as 18-(substituted phenyl)-19,20-dinor-$PGI_1$-type compounds.

When $R_7$ is

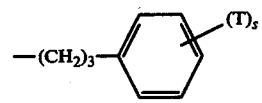

wherein T and s are as defined above, the novel compounds herein are named as 19-phenyl-20-nor-$PGI_1$-type compounds, when s is zero. When s is one, 2, or 3, the corresponding compounds are named as 19-(substituted phenyl)-20-nor-$PGI_1$-type compounds.

When $R_7$ is

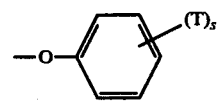

wherein T and s are as defined above, and neither $R_3$ nor $R_4$ is methyl, the novel compounds herein are named as 16-phenoxy-17,18,19,20-tetranor-$PGI_1$-type compounds, when s is zero. When s is one, 2, or 3, the corresponding compounds are named as 16-(substituted phenoxy)-17,18,19,20-tetranor-$PGI_1$-type compounds. When one and only one of $R_3$ and $R_4$ is methyl or both $R_3$ and $R_4$ are methyl, then the corresponding compounds wherein $R_7$ is as defined in this paragraph are named as 16-phenoxy- or 16-(substituted phenoxy)-18,19,20-trinor-$PGI_1$-type compounds or 16-methyl-16-phenoxy- or 16-(substituted phenoxy)-18,19,20-trinor-$PGI_1$-type compounds, respectively.

When at least one of $R_3$ and $R_4$ is not hydrogen, then (except for the 16-phenoxy or 16-phenyl compounds discussed above), there are thusly described the 16-methyl-$PGI_1$-type (one and only one of $R_3$ and $R_4$ is methyl), 16,16-dimethyl-$PGI_1$-type ($R_3$ and $R_4$ are both methyl), 16-fluoro-$PGI_1$-type (one and only one of $R_3$ and $R_4$ is fluoro), and 16,16-difluoro-$PGI_1$-type ($R_3$ and $R_4$ are both fluoro) compounds. For those compounds wherein $R_3$ and $R_4$ are different, the prostaglandin analogs so represented contain an asymmetric carbon atom at C-16. Accordingly, two epimeric configurations are possible: "(16S)" and "(16R)". Further, there is described by this invention the C-16 epimeric mixture: "(16RS)".

When $X_1$ is —$CH_2OH$, the novel compounds herein are named as 2-decarboxy-2-hydroxymethyl-$PGI_1$-type compounds.

When $X_1$ is —$COL_4$, the novel compounds herein are named as $PGI_1$-type, amides. Further, when $X_1$ is —$COOR_{10}$, the novel compounds herein are named as $PGI_1$-type, esters and $PGI_1$-type, salts.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tertbutylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-naphthylethyl), and 1-(2-naphthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of

wherein T is alkyl of one to 3 carbon atoms, inclusive, fluoro, chloro, trifluoromethyl, or alkoxy of one to 3 carbon atoms, inclusive; and s is zero, one, 2, or 3, with the proviso that not more than two T's are other than alkyl, are phenyl, (o-, m-, or p-)tolyl, (o-, m-, or p-)ethylphenyl, 2-ethyl-p-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-trimethylphenyl, (o-, m-, p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-(dichlorophenyl, 4-chloro-3-fluorophenyl, (3-, or 4-(chloro-2-fluorophenyl, o-, m-, or p-trifluoromethylphenyl, (o-, m-, or p-methoxyphenyl, (o-, m-, or p-)-ethoxyphenyl, (4- or 5-)chloro-2-methoxyphenyl, and 2,4-dichloro(5- or 6-)methylphenyl.

Examples of phenyl esters substituted in the para position (i.e., $X_1$ is —$COOR_{10}$, $R_{10}$ is p-substituted phenyl) include p-acetamidophenyl ester, p-benzamidophenyl ester, p-(p-acetamidobenzamido)phenyl ester, p-(p-benzamidobenzamido)phenyl ester, p-amidocarbonylamidophenyl ester, p-acetylphenyl ester, p-benzylphenyl ester, p-amidocarbonylphenyl ester, p-methoxycarbonylphenyl ester, p-benzoyloxyphenyl ester, p-(p-acetamidobenzoyloxy)phenyl ester, and p-hydroxybenzaldehyde semicarbazone ester.

Examples of novel prostacyclin amides herein (i.e., $X_1$ is —$COL_4$) include the following:

(1) Amides within the scope of alkylamino groups of the formula —$NR_{21}R_{22}$ are methylamide, ethylamide, n-propylamide, n-butylamide, n-pentylamide, n-hexylamide, n-heptylamide, n-octylamide, n-nonylamide, n-decylamide, n-undecylamide and n-dodecylamide, and isomeric forms thereof. Further examples are dimethylamide, diethylamide, di-n-propylamide, di-n-butylamide, methylethylamide, methylpropylamide, methylbutylamide, ethylpropylamide, ethylbutylamide, and propylbutylamide. Amides within the scope of cycloalkylamino are cyclopropylamide, cyclobutylamide, cyclopentylamide, 2,3-dimethylcyclopentylamide, 2,2-dimethylcyclopentylamide, 2-methylcyclopentylamide, 3-tert-butylcyclopentylamide, cyclohexylamide, 4-tert-butylcyclohexylamide, 3-isopropylcyclohexylamide, 2,2-dimethylcyclohexylamide, cycloheptylamide, cyclooctylamide, cyclononylamide, cyclodecylamide, N-methyl-N-cyclobutylamide, N-methyl-N-cyclopentylamide, N-methyl-N-cyclohexylamide, N-ethyl-N-cyclopentylamide, N-methyl-N-cyclohexylamide, dicyclopentylamide, and dicyclohexylamide. Amides within the scope of aralkylamino are benzylamide, 2-phenethylamide, 2-phenylethylamide, N-methyl-N-benzylamide, and dibenzylamide. Amides within the scope of substituted phenylamino are p-chloroanilide, m-chloroanilide, 2,4-dichloroanilide, 2,4,6-trichloroanilide, m-nitroanilide, p-nitroanilide, p-methoxyanilide, 3,4-dimethoxyanilide, 3,4,5-trimethoxyanilide, p-hydroxymethylanilide, p-methylanalide, m-methylanilide, p-ethylanilide, t-butylanilide, p-carboxyanilide, p-methoxycarbonylanilide, o-carboxyanilide and o-hydroxyanilide. Amides within the scope of carboxyalkylamino are carboxymethylamide, carboxyethylamide, carboxypropylamide, and carboxybutylamide. Amides within the scope of carbamoylalkylamino are carbamoylmethylamide, carbamoylethylamide, carbamoylpropylamide, and carbamoylbutylamide. Amides within the scope of cyanoalkylamino are cyanomethylamide, cyanoethylamide, cyanopropylamide, and cyanobutylamide. Amides within the scope of acetylalkylamino are acetylmethylamide, acetylethylamide, acetylpropylamide, and acetylbutylamide. Amides within the scope of acetylalkylamido are acetylmethylamide, acetylethylamide, acetylpropylamide, and acetylbutylamide. Amides within the scope of benzoylalkylamino are benzoylmethylamide, benzoylethylamide, benzoylpropylamide, and benzoylbutylamide. Amides within the scope of substituted benzoylalkylamino are p-chlorobenzoylmethylamide, m-chlorobenzoylmethylamide, 2,4-dichlorobenzoylmethylamide, 2,4,6-trichlorobenzoylmethylamide, m-nitrobenzoylmethylamide, p-nitrobenzoylmethylamide, p-methoxybenzoylmethylamide, 2,4-dimethoxybenzoylmethylamide, 3,4,5-trimethoxybenzoylmethylamide, p-hydroxymethylbenzoylmethylamide, p-methylbenzoylmethylamide, m-methylbenzoylmethylamide, p-ethylbenzoylmethylamide, t-butylbenzoylmethylamide, p-carboxybenzoylmethylamide, m-methoxycarbonylbenzoylamide, o-carboxybenzoylmethylamide, o-hydroxybenzoylmethylamide, p-chlorobenzoylethylamide, m-chlorobenzoylethylamide, 2,4-dichlorobenzoylethylamide, 2,4,6-trichlorobenzoylethylamide, m-nitrobenzoylethylamide, p-nitrobenzoylethylamide, p-methoxybenzoylethylamide, p-methoxybenzoylethylamide, 2,4-dimethoxybenzoylethylamide, 3,4,5-trimethoxybenzoylethylamide, p-hydroxymethylbenzoylethylamide, p-methylbenzoylethylamide, m-methylbenzoylethylamide, p-ethylbenzoylethylamide, t-butylbenzoylethylamide, p-carboxybenzoylethylamide, m-methoxycarbonylbenzoylethylamide, o-carboxybenzoylethylamide, o-hydroxybenzoylethylamide, p-chlorobenzoylpropylamide, m-chlorobenzoylpropylamide, 2,4-dichlorobenzoylpropylamide, 2,4,6-trichlorobenzoylpropylamide, m-nitrobenzoylpropylamide, p-nitrobenzoylpropylamide, p-methoxybenzoylpropylamide, 2,4-dimethoxybenzoylpropylamide, 3,4,5-trimethoxybenzoylpropylamide, p-hydroxymethylbenzoylpropylamide, p-methylbenzoylpropylamide, m-methylbenzoylpropylamide, p-ethylbenzoylpropylamide, t-butylbenzoylpropylamide, p-carboxybenzoylpropylamide, m-methoxycarbonylbenzoylpropylamide, o-carboxybenzoylpropylamide, o-hydroxybenzoylpropylamide, p-chlorobenzoylbutylamide, m-chlorobenzoylbutylamide, 2,4-dichlorobenzoylbutylamide, 2,4,6-trichlorobenzoylbutylamide, m-nitrobenzoylmethylamide, p-nitrobenzoylbutylamide, p-methoxybenzoylbutylamide, 2,4-dimethoxybenzoylbutylamide, 3,4,5-trimethoxybenzoylbutylamide, p-hydroxymethylbenzoylbutylamide, p-methylbenzoylbutylamide, m-methylbenzoylbutylamide, p-ethylbenzoylbutylamide, m-methylbenzoylbutylamide, p-ethylbenzoylbutylamide, t-butylbenzoylbutylamide, p-carboxybenzoylbutylamide, m-methoxycarbonylbenzoylbutylamide, o-carboxybenzoylbutylamide, o-hydroxybenzoylmethylamide. Amides within the scope of pyridylamino are α-pyridylamide, β-pyridylamide, and γ-pyridylamide. Amides within the scope of substituted pyridylamino are 4-methyl-α-pyridylamide, 4-methyl-β-pyridylamide, 4-chloro-α-pyridylamide, and 4-chloro-β-pyridylamide. Amides within the scope of pyridylalkylamino are α-pyridylmethylamide, β-pyridylmethylamide, γ-pyridylmethylamide, α-pyridylethylamide, β-pyridylethylamide, γ-pyridylethylamide, α-pyridylpropylamide, β-pyridylpropylamide, γ-pyridylpropylamide, α-pyridylbutylamide, β-pyridylbutylamide, and γ-pyridylbutylamide. Amides within the scope of substituted pyridylalkylamino are 4-methyl-α-pyridylmethylamide, 4-methyl-β-pyridylmethylamide, 4-chloro-α-pyridylmethylamide, 4-chloro-β-pyridylmethylamide, 4-methyl-α-pyridylethylamide, 4-methyl-β-pyridylethylamide, 4-chloro-α-pyridylethylamide, 4-chloro-β-pyridylethylamide, 4-methyl-α-pyridylpropylamide, 4-methyl-β-pyridylpropylamide, 4-chloro-α-pyridylpropylamide, 4-chloro-β-pyridylpropylamide, 4-methyl-α-pyridylbutylamide, 4-methyl-β-pyridylbutylamide, 4-chloro-α-pyridylbutylamide, and 4-chloro-β-pyridylbutylamide. Amides within the scope of hydroxyalkylamino are hydroxymethylamide, α-hydroxyethylamide, β-hydroxyethylamide, α-hydroxypropylamide, β-hydroxypropylamide, γ-hydroxypropylamide, 1-(hydroxymethyl)ethylamide, 1-(hydroxymethyl)propylamide, (2-hydroxyethyl)propylamide, and α,α-dimethyl-β-hydroxyethylamide. Amides within the scope of dihydroxyalkylamino are dihydroxymethylamide, α,α-dihydroxyethylamide, α,β-dihydroxyethylamide, β,β-dihydroxyethylamide, α,α-dihydroxypropylamide, α,β-dihydroxypropylamide, α,γ-dihydroxypropylamide, β,β-dihydroxypropylamide, β,γ-dihydroxypropylamide, γ,γ-dihydroxypropylamide, 1-(hydroxymethyl)2-hydroxyethylamide, 1-(hydroxymethyl)1-hdroxyethylamide, α,α-dihydroxybutylamide, α,β-dihydroxybutylamide, α,γ-dihydroxybutylamide, α,δ-dihydroxybutylamide, β,β-dihydroxybutylamide, β,γ-dihydroxybutylamide, β,δ-dihydroxybutylamide, γ,γ-dihydroxybutylamide, γ,δ-dihydroxybutylamide, δ,δ-dihydroxybutylamide, and 1,1-bis(hydroxymethyl)ethylamide. Amides within the scope of trihydroxyalkylamino are tris(hydroxymethyl)methylamide and 1,3-dihydroxy-2-hydroxymethylpropylamide.

(2) Amides within the scope of the cycloamino groups described above are pyrrolidylamide, piperidylamide, morpholinylamide, hexamethyleneiminylamide, piperazinylamide, pyrrolinylamide, and 3,4-didehydropiperidinylamide.

(3) Amides within the scope of carbonylamino of the formula $-NR_{23}COR_{21}$ are methylcarbonylamide, ethylcarbonylamide, phenylcarbonylamide, and benzylcarbonylamide, Amides within the scope of sulfonylamino of the formula $-NR_{23}SO_2R_{21}$ are methylsulfonylamide, ethylsulfonylamide, phenylsulfonylamide, p-tolylsulfonylamide, benzylsulfonylamide.

(4) Hydrazines within the scope of the above hydrazino groups are hydrazine, N-aminopiperidine, benzoylhydrazine, phenylhydrazine, N-aminomorpholine, 2-hydroxyethylhydrazine, methylhydrazine, 2,2,2-hydroxyethylhydrazine and p-carboxyphenylhydrazine.

The term "pharmacologically acceptable cation" refers to those pharmacologically acceptable salts of the prostacyclintype carboxylic acids which are conventionally employed with prostaglandins. In particular, such pharmacologically acceptable salts include pharmacologically acceptable metal cations, amine cations, and quarternary ammonium cations. Additionally basic amino acids such as arginine and lysine are employed. Further, certain amine cations such as THAM [tris(hydroxymethyl)amino methyl] and adamantanamine are especially useful for the present purposes. Additionally, U.S. Pat. No. 4,016,184, issued Apr. 5, 1977 (particularly column 29), describes salts which are likewise preferred for the present purposes.

The novel prostacyclin analogs disclosed herein produce a multiplicity of biological responses, rendering these compounds useful for a variety of pharmacological purposes. In particular, the biological responses include platelet aggretation, inhibition, smooth muscle stimulation, blood pressure lowering, gastric secretion reduction, NOSAC (non-steroidal antiinflammatory compound)-induced lesion inhibition, bronchodilation, nasal decongestion, peripheral vascular circulatory improvement, reproduction and fertility control, renal blood flow alteration, dermatosis reversal, inflammation reduction, and intraocular pressure reduction.

Accordingly, the novel prostacyclin analogs of the present invention are used as agents in the study, prevention, control, and treatment of diseases, and other undesirable physiological conditions, in mammals, particularly humans, valuable domestic animals, pets, zoological specimens, and laboratory animals (e.g., mice rats, rabbits and monkeys), as follows:

(a) Platelet Aggregation Inhibition.

These novel prostacyclin analogs are useful whenever it is desired to inhibit platelet aggregation, to reduce the adhesive character of platelets, or to remove or prevent the formation of thrombi in mammals, including man. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.01 to about 10 mg. per kg. of body weight per day are used, the exact dose depending on the age, weight, and condition of the patient or animal, and on the frequency and route of administration.

The preferred dosage form for these compounds is oral, although other non-parenteral routes (e.g., buccal, rectal, sublingual) are likewise employed in preference to parenteral routes. Oral dosage forms are conventionally formulated (tablets, capsules, et cetera) and administered 2 to 4 times daily. Doses in the range of about 0.05 to 100 mg./kg. of body weight per day are effective.

The addition of these compounds to whole blood provides in vitro applications such as, storage of whole blood to be used in heart-lung machines. Additionally whole blood containing these compounds can be circulated through organs, e.g., heart and kidneys, which have been removed from a donor prior to transplant. They are also useful in preparing platelet rich concentrates for use in treating thrombocytopenia, chemotherapy, and radiation therapy. In vitro applications utilize a dose of 0.001–1.0 $\mu$g/ml. of whole blood.

(b) Smooth Muscle Stimulation

The novel prostacyclin analogs herein are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, they are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the compound is administered by intravenous infusion immediately after abortion or delivery at a dose in the range about 0.01 to about 50 $\mu$g. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight and condition of the patient or animal.

(c) Blood Pressure Lowering

The novel prostacyclin analogs herein are useful as hypotensive agents to reduce blood pressure in mammals, including man. For this purpose, the compounds are administered by intravenous infusion at the rate of about 0.01 to about 50 $\mu$g. per kg. of body weight per minute or in single or multiple doses of about 25 to 500 $\mu$g. per kg. of body weight total per day.

As for antithrombic application described above, these compounds are most preferrably administered orally or by other convenient non-parenteral dosage form. In determining the appropriate oral dosage and frequency of administration, titration of dose in conjunction with other antihypertensive drugs being concomitantly administered is required. When used as the sole antihypertensive agent, determining the minimum effective dose required for adequate control of blood pressure is undertaken by initiating therapy at or near the threshold dose of patent or animal response. Thereafter upward adjustment of the dosage, until full control is achieved or undesired side effects are observed, is undertaken. Accordingly, threshold dosages of 0.01 to 1.0 mg./kg. of body weight are employed.

(d) Gastric Secretion Reduction

These novel prostacyclin analogs are also useful in mammals, including man and certain useful animals, e.g., dogs and pigs, to reduce and control gastric secretion, thereby reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 $\mu$g. to about 20 $\mu$g. per kg. of body weight per minute, or in a total daily dose by injection or infusion in the range about 0.01 to about 10 mg. per kg. of body weight per day, the exact dose depending on the age, weight, and condition of the patient or animal, and on the frequency and route of administration.

Preferably, however, the novel prostacyclin analogs are administered orally or by other non-parenteral routes. As employed orally, one to 6 administrations daily in a dosage range of about 1.0 to 100 mg./kg. of body weight per day is employed. Once healing of the ulcers has been accomplished the maintenance dosage required to prevent recurrence is adjusted downward so long as the patient or animal remains asymptomatic.

(e) NOSAC-Induced Lesion Inhibition

These novel prostacyclin analogs herein are also useful in reducing the undesirable gastrointestinal effects resulting from systemic administration of anti-inflammatory prostaglandin synthetase inhibitors, and are used for that purpose by concomitant administration of the prostaglandin derivative and the anti-inflammatory prostaglandin synthetase inhibitor. See Partridge et al., U.S. Pat. No. 3,781,429, for a disclosure that the ulcerogenic effect induced by certain non-steroidal anti-inflammatory agents in rats is inhibited by concomitant oral administration of certain prostaglandins. Accordingly these novel prostacyclin analogs herein are useful, for example, in reducing the undesirable gastrointestinal effects resulting from systemic administration of indomethacin, phenylbutazone, and aspirin. These are substances specifically mentioned in Partridge et al. as nonsteroidal, anti-inflammatory agents. These are also known to be prostaglandin synthetase inhibitors.

The anti-inflammatory synthetase inhibitor, for example indomethacin, aspirin, or phenylbutazone is administered in any of the ways known in the art to alleviate an inflammatory condition, for example, in any dosage regimen and by any of the known routes of systemic administration.

The prostacyclin analog is administered along with the anti-inflammatory prostaglandin synthetase inhibitor either by the same route of administration or by a different route. For example, if the antiinflammatory substance is being administered orally, the novel prostacyclin analog is also administered orally, or, alternatively, is administered rectally in the form of a suppository or, in the case of women, vaginally in the form of a suppository or a vaginal device for slow release, for example as described in U.S. Pat. No. 3,545,439. Alternatively, if the antiinflammatory substance is being administered rectally, the novel prostacyclin analog is also administered rectally. Further, the novel prostacyclin analog can be conveniently administered orally or, in the case of women, vaginally. It is especially convenient when the administration route is to be the same for both antiinflammatory substance and novel prostacyclin analog, to combine both into a single dosage form.

The dosage regimen for the novel prostacyclin analog in accord with this treatment will depend upon a variety of factors, including the type, age, weight, sex and medical condition of the mammal, the nature and dosage regimen of the antiinflammatory synthetase inhibitor being administered to the mammal, the sensitivity of the particular prostacyclin analog to be administered. For example, not every human in need of an antiinflammatory substance experiences the same adverse gastrointestinal effects when taking the substance. The gastrointestinal effects will frequently vary substantially in kind and degree. But it is within the skill of the attending physician or veterinarian to determine that administration of the antiinflammatory substance is causing undesirable gastrointestinal effects in the human or animal subject and to prescribe an effective amount of the novel prostacyclin analog to reduce and then substantially to eliminate those undesirable effects.

(f) Bronchodilation (Antiasthma)

These novel prostacyclin analogs are also useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostacyclin analogs can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone).

These compounds are effectively administered to human asthma patients by oral inhalation or by aerosol inhalation. For administration by the oral inhalation route with conventional nebulizers or by oxygen aerosolization it is convenient to provide the instant active ingredient in dilute solution, preferably at concentrations of about one part of medicament to form about 100 to 200 parts by weight of total solution. Entirely conventional additives may be employed to stabilize these solutions or to provide isotonic media, for example, sodium chloride, sodium citrate, citric acid, sodium bisulfite, and the like can be employed. For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Instead of a co-solvent there can also be used a dispensing agent such as ethyl alcohol. Suitable means to employ the aerosol inhalation therapy technique are described fully in U.S. Pat. No. 2,868,691, for example.

(g) Nasal Decongestion

The novel prostacyclin analogs herein are useful in mammals, including man, as nasal decongestants and are used for this purpose in a dose range of about 10 μg. to about 10 mg. per ml. of a pharmacologically suitable liquid vehicle or as an aerosol spray, both for topical application.

(h) Peripheral Vascular Circulatory Improvement.

These compounds are also useful in treating peripheral vascular disease in humans. The term peripheral vascular disease as used herein means disease of any of the blood vessels outside of the heart and disease of the lymph vessels, for example, frostbite, ischemic cerebrovascular disease, artheriovenous fistulas, ischemic leg ulcers, phlebitis, venous insufficiency, gangrene, hepatorenal syndrome, ductus arteriosus, non-obstructive mesenteric ischemia, arteritis lymphangitis and the like. These examples are included to be illustrative and should not be construed as limiting the term peripheral vascular disease. For these conditions the compounds of this invention are administered orally or parenterally via injection or infusion directly into a vein or artery, intravenous or intraarterial injections being preferred. The dosages of these compounds are in the range of 0.01–1.0 μg./kg. of body weight administered by infusions at an hourly rate or by injection on a daily basis, i.e., 1–4 times a day, the exact dose depending on the age, weight, and condition of the patient and on the frequency and route of administration. Corresponding oral doses are in the range 0.05–50 mg. every 2 hrs. during up to a maximum of 6 administrations daily. Treatment is continued for one to five days, although three days is ordinarily sufficient to assure long-lasting therapeutic action. In the event that systemic or side effects are observed, the dosage is lowered below the threshold at which such systemic or side effects are observed.

(i) Reproduction and Fertility Control.

The novel prostacyclin analogs herein are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 μg. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral, or other parenteral routes (e.g., intramuscular).

These compounds are further useful for controlling the reproductive cycle in menstruating female mammals, including humans. By the term menstruating female mammals is meant animals which are mature enough to menstruate, but not so old that regular menstruation has ceased. For that purpose the compound is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine routes are alternate methods of administration. Additionally, expulsion of an embryo or a fetus is accomplished by similar administration of the compound during the first or second trimester of the normal mammalian gestation period.

These compounds are further useful in causing cervical dilation in pregnant and nonpregnant female mammals for purposes of gynecology and obstetrics. In labor induction and in clinical abortion produced by these compounds, cervical dilation is also observed. In cases of infertility, cervical dilation produced by these compounds is useful in assisting sperm movement to the uterus. Cervical dilation by these compounds is also useful in operative gynecology such as D and C (Cervical Dilation and Uterine Curettage) where mechanical dilation may cause perforation of the uterus, cervical tears, or infections. It is also useful for diagnostic procedures where dilation is necessary for tissue examination. For these purposes, these compounds are administered locally or systemically.

These compounds, for example, are administered orally or vaginally at doses of about 5 to 50 mg. per treatment of an adult female human, with from one to five treatments per 24 hour period. Alternatively these compounds are administered intramuscularly or subcutaneously at doses of about one to 25 mg. per treatment. The exact dosages for these purposes depend on the age, weight, and condition of the patient or animal.

These compounds are further useful in domestic animals (1) as an abortifacient (especially for feedlot heifers), (2) as an aid to estrus detection, and (3) as regulators of the estrus. Domestic animals include horses, cattle, sheep, and swine. The regulation or synchronization of estrus allows for more efficient management of both conception and labor by enabling a herdsman to breed all female animals in short, pre-defined intervals. This synchronization results in a higher percentage of live births than the percentage achieved by natural control and, moreover, is especially important in facilitating artificial insemination (AI), by permitting a more economic insemination operation. These compounds are injected or applied in a feed at doses of 0.1–100 mg. per animal and may be combined with other agents such as steroids. Dosing schedules will depend on the species treated. For example, mares are given these compounds 5 to 8 days after ovulation and return to estrus. Cattle are likewise treated after ovulation, but may thereafter require an additional administration to advantageously bring all into estrus at the same time.

(j) Renal Blood Flow Alteration

The novel prostacyclin analogs herein increase the flow of blood in the mammalian kidney, thereby increasing volume and electrolyte content of the urine. For that reason, these compounds are useful in managing cases of renal dysfunction, especially those involving blockage of the renal vascular bed. Illustratively, these compounds are useful to alleviate and correct cases of edema resulting, for example, from massive surface burns, and in the management of shock. For these purposes, these compounds are preferably first administered by intravenous injection at a dose in the range 10 to 1000 $\mu$g. per kg. of body weight or by intravenous infusion at a dose in the range 0.1 to 20 $\mu$g. per kg. of body weight per minute until the desired effect is obtained. Subsequent doses are given by intravenous, intramuscular, or subcutaneous injection or infusion in the range 0.05 to 2 mg. per kg. of body weight per day.

(k) Dermatosis Reversal

These novel prostacyclin analogs are useful for treating proliferating skin diseases of man and domesticated animals, including psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun-induced keratosis, non-malignant keratosis, acne, and seborrheic dermatitis in humans and atopic dermatitis and mange in domesticated animals. These compounds alleviate the symptoms of these proliferative skin diseases: psoriasis, for example, being alleviated when a scale-free psoriasis lesion is noticeably decreased in thickness and noticeably, but incompletely cleared, or completely cleared.

For these purposes, these compounds are applied topically as compositions including a suitable pharmaceutical carrier, for example as an ointment, lotion, paste, jelly, spray, or aerosol, using topical bases such as petrolatum, lanolin, polyethylene glycols, and alcohols. These compound, as the active ingredients, constitute from about 0.1% to about 15% by weight of the composition, preferably from about 0.5% to about 2%. In addition to topical administration, injection may be employed, as intradermally, intra- or peri-lesionally, or subcutaneously, using appropriate sterial saline compositions.

(l) Inflammation Reduction

The novel prostacyclin analogs herein are useful as antiinflammatory agents for inhibiting chronic inflammation in mammals including the swelling and other unpleasant effects thereof using methods of treatment and dosages generally described for the therapeutic agents in U.S. Pat. No. 3,885,041, which patent is incorporated herein by reference.

(m) Reduction of Intraocular Pressure

The novel prostacyclin analogs herein are finally useful in man for the reduction of intraocular pressure in those disease states where abnormally elevated pressure in the eye is a threat to the sight of the patient (i.e., glaucoma). While many routes of administration are successfully employed for this purpose, direct application of a sterile ophthalmic solution (e.g., in the form of drops) is the preferred route for convenience and minimization of systemic effects. While ultimate dosage is readily determined by patient response in the exhibition of significantly lower intraocular pressure and the absence of localized side effects, such as irritation of eye tissues, initial dosage levels of about 0.05 mg. to 50 mg. per several drops of sterile ophthalmic solution, repeated 2 to 4 times per day, are employed.

The novel prostacyclin analogs herein are thus surprisingly and unexpectedly useful for a wide variety of pharmacological purposes, rendering these compounds pharmacological as well as structural analogs of prostacyclin. Moreover, the prostacyclin analogs herein exhibit a more prolonged chemical stability, facilitating their formulation and use as pharmacological agents. Finally, these novel prostacyclin analogs exhibit improved utility as compared to prostacyclin when employed, as described above, as antithrombotic, antiasthma, or antiinflammatory agents. This improved utility is evidenced in that the novel prostacyclin analogs of this invention exhibit increased potency or selectivity of action, thus exhibiting fewer undesirable side effects when administered for one of these preferred pharmacological uses.

Within the scope of the novel prostacyclin analogs described above, certain compounds are preferred in that they exhibit increased potency, selectivity of action, or otherwise represent especially convenient and useful agents, especially for the preferred uses described above.

Accordingly, preferred compounds are those wherein $Z_1$ is —$(CH_2)_g$—$(CH_2)_2$—$CH_2$—. Further, g is preferably the integer one or 3, most preferably being one. With respect to the $Y_1$ moiety, preferred compounds are those wherein $Y_1$ is trans—CH=CH—, —$CH_2CH_2$— or —C≡C—, the most especially preferred compounds being those wherein $Y_1$ is trans—CH=CH—.

With respect to the $L_1$ moiety, those compounds wherein $R_3$ and $R_4$ are the same are preferred. Further preferred are those compounds herein wherein at least $R_3$, $R_4$, and $R_5$ is hydrogen. In the event $Y_1$ is cis-CH=CH— or —C≡C—, compounds wherein $R_3$, $R_4$, and $R_5$ are all hydrogen are preferred.

With respect to the integers m, h, and s, it is preferred that m be the integer 3, h be the integer zero or one and s be the integer zero or one. Further, T is preferably chloro, fluoro, or trifluoromethyl.

Further preferred are the carboxylic acids or derivatives, i.e., esters, especially the p-substituted phenyl esters, and amides. With respect to the novel amides herein, preferred compounds are those wherein $R_{21}$ and $R_{22}$ are preferably hydrogen or alkyl of one to 8 carbon atoms, inclusive, being the same or different, preferably with the total number of carbon atoms in $R_{21}$ and $R_{22}$ being less than or equal to 8. More especially preferred are those amides wherein $R_{21}$ and $R_{22}$ are hydrogen or alkyl of one to 4 carbon atoms, inclusive, being the same or different, with the total number of carbon atoms in $R_{21}$ and $R_{22}$ being less than or equal to 4. Further, $R_{23}$ is preferably hydrogen.

The chart herein describes the method by which the novel prostacyclin analogs herein are prepared from known or readily synthesized starting materials.

With respect to Chart A, g, $L_1$, $M_1$, $R_7$, $R_8$, $X_1$, $X_2$, and $Z_1$ are as defined above.

CHART A

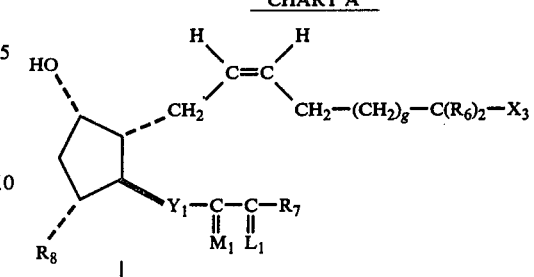

XXI

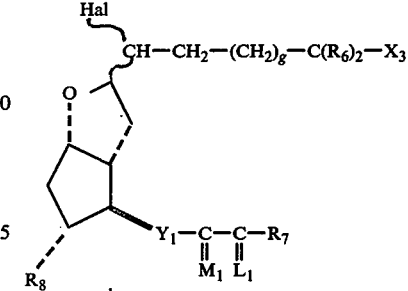

XXII

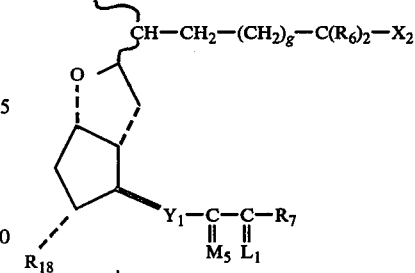

XXIII

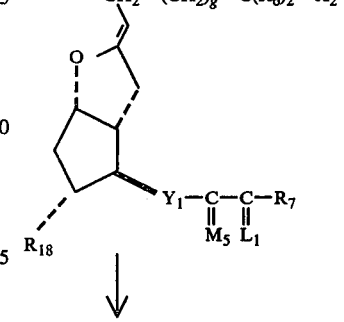

XXIV

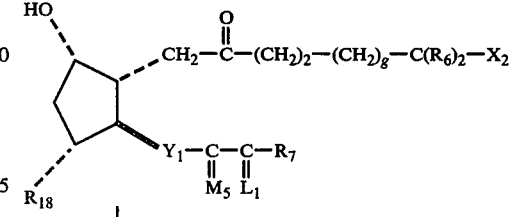

XXV

-continued
CHART A

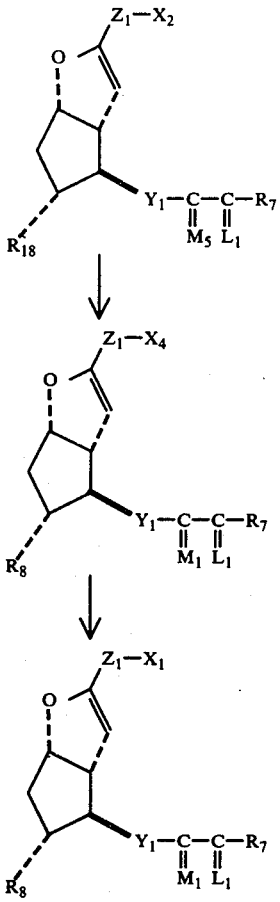

$X_3$ is
(1) —$COOR_2$, wherein $R_2$ is as defined above;
(2) —$CH_2OH$;
(3) —$CH_2NL_2L_3$; or
(4) —$COL_4$, wherein $L_4$ is as defined above.

$X_4$ is
(1) —$COOR_{11}$, wherein $R_{11}$ is an alkali metal salt;
(2) —$CH_2OH$;
(3) —$CH_2NL_2L_3$, wherein $L_2$ and $L_3$ are as defined above; or
(4) —$COL_4$, wherein $L_4$ is as defined above.

$R_6$ is hydrogen or fluoro and Hal is bromo or iodo.

Further with respect to Chart A the formula XXI compound is known in the art or prepared by methods known in the art. Specifically, formula XXI compounds are $PGF_2\alpha$-type compounds in the form of esters, amides, primary alcohols, or amines. Moreover, such compounds are all prepared from readily available starting materials by methods known in the art.

The formula XXII compound is prepared from the formula XXI compound by halocyclization. When Hal is iodo, this halocyclization proceeds by reacting the formula XXI compound with potassium iodide or an alkali metal carbonate or bicarbonate in an organic system containing iodide. In the latter case solvents such as methylene chloride can be employed. Further, reaction temperatures at or below ambient temperature, preferably at about 0° C., are employed. The resulting reaction mixture is then quenched by addition of sodium sulfate and sodium carbonate, yielding the formula XXII iodo compound.

When Hal is bromo, a convenient cyclobrominating agent is N-bromosuccinimide. Solvents such as methylene chloride are employed and the reaction proceeds from about 0° C. to ambient temperature. When recovery of the pure formula XXII product is desired, chromatographic methods for isolation of the pure form are employed. High pressure liquid chromatography is an especially useful technique for such an isolation.

The formula XXIII compound is then prepared from the formula XXII compound by alkanoylation of the various free hydroxyl groups of the formula XXII compound. This alkanoylation proceeds at or about ambient temperature in the presence of an amine base (e.g., pyridine) and the alkanoic anhydride corresponding to the alkanoate to be prepared. For example, in preparing the formula XXIII acetates, acetic anhydride in pyridine are employed for this purpose. Under the mild conditions described above, the alkanoate formation is ordinarily complete within several hours to several days.

Thereafter, the formula XXIV compound is prepared from the formula XXIII compound by dehydrohalogenation with base. Numerous organic bases are known to be useful for this purpose. For example, potassium t-butoxide and 1,5-diazabicyclo-[5.4.0] undec-5-ene-(DBU) are employed.

This formula XXIV $PGI_2$-type intermediate is then transformed to the corresponding formula XXV 6-oxo-$PGF_1\alpha$-type compound by hydrolysis under mild acidic conditions. For example, mixtures of acetic acid, tetrahydrofuran and water are employed in the hydrolysis reaction. The formula XXV product is then isolated from the resulting mixture of hydrolysis products by conventional means (e.g., column chromatography).

This formula XXV compound is then recyclized to the formula XXVI 6,7-didehydro-$PGI_1$-type intermediate by refluxing in benzene or a similar monocyclic or bicyclic, substantially non-polar aromatic solvent. The formula XXVI 6,7-didehydro-$PGI_1$-type intermediate is then recovered from the reaction mixture by chromatography or similar conventional isolation techniques. When a chromatographic separation of products is employed, care must be taken to avoid acidic, especially aqueous acidic eluents. Thus, for example, a preferred eluent for this purpose is ethyl acetate is Skellysolve B containing a small amount (e.g., less than 1%) of an amine base such as triethylamine. The above-described isolation technique thus permits the recovery of the desired formula XXVI 6,7-didehydro-$PGI_1$ isomer from other contaminants, principally the corresponding $PGI_2$-type, alkanoates.

The formula XXVII prostacyclin analogs are then prepared from the formula XXVI compound by dealkanoylation. For this purpose, a convenient saponifying agent is an alkali metal methoxide in methanol. When the saponification is complete, the formula XXVII product is then recovered from the reaction mixture by conventional means. For example, suitable recovery techniques comprise concentration under reduced pressure to yield the formula XXVII product.

The formula XXVII product is obtained as a primary alcohol, amine, or amide, according to the selection of formula XXI starting material. However, when a formula XXI ester is employed, the corresponding formula XXVII alkali metal salt is obtained. These salts are transformed to the formula XXVIII esters by esterification techniques known in the art. For example, one readily adaptable technique for preparing the various esters according to $X_1$ of the formula XXVIII compound is reported by Mukaiyama, Chem. Letters 1975:1045. By this method, the formula XXVII alkaline metal salt is first dissolved in dimethylformamide and the resulting mixture stirred at ambient temperature with N-methyl-2-bromo-pyridinium iodide for several hours. Thereupon, the alcohol corresponding to the desired ester, dissolved in trimethylamine, is added and the esterification proceeds expeditiously. When the reaction is complete, the desired product is recovered by conventional techniques.

In preparing the various formula XXVIII pharmacologically acceptable salts, aside from the alkaline metal salts of formula XXVII, the formula XXVII compound is first acidified to the free acid and then rapidly extracted into diethyl ether. This ethereal solution is then reacted with an aqueous solution containing the base corresponding to the desired formula XXVIII salt. When the resulting neutralization is complete, the formula XXVIII salt is then recovered by the conventional means (e.g., solvent evaporation).

Returning to the formula XXI compound, prostaglandin analogs of this description are, as indicated above, known in the art and are alternatively prepared by methods known in the art. For examples of such known compounds and such methods of preparation, see U.S. Pat. Nos. 3,987,072, describing 11-deoxy-PG-type compounds; 3,950,363, describing 11-deoxy-11-hydroxymethyl prostaglandin analogs; 4,026,909, describing cis-13-PG compounds; 4,029,618, describing 13,14-didehydro-PG compounds; 3,728,382, describing 15-methyl-PG-type compounds; 3,903,131, describing 16-methyl prostaglandin analogs; 3,969,380, describing 16-fluoro prostaglandin analogs; 3,987,087, describing 17-phenyl prostaglandin analogs; 3,864,387, describing 16-phenoxy-PG-type compounds; 4,001,300, describing 2,2-difluoro-PG-type compounds; 4,028,419, describing 2-decarboxy-2-hydroxymethyl-PG-type compounds; 3,894,062, describing aromatic esters of PG-type compounds; U.S. Ser. No. 719,055, describing 2-decarboxy-2-aminomethyl-PG-type compounds; U.S. Pat. Nos. 3,981,868, describing amido and cycloamido derivatives of PG-type compounds; and 3,954,741, describing carbonylamido and sulfonylamido PG-type compounds.

DESCRIPTION OF THE PREFERRED EMBODIMENTS

The invention can be more fully understood by the following examples and preparations.

All temperatures are in degrees centigrate.

IR (infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60D, or T-60 spectrophotometer in deuterochloroform solutions with tetramethylsilane as an internal standard (downfield).

Mass spectra are recorded on an CEG model 110B Double Focusing High Resolution Mass Spectrometer on an LKB Model 9000 Gas-Chromatograph-Mass Spectrometer. Trimethylsilyl derivatives are used, except where otherwise indicated.

"Brine", herein, refers to an aqueous saturated sodium chloride solution.

The A-IX solvent system used in thin layer chromatography is made up from ethyl acetate-acetic acid-2,2,4-trimethylpentane-water (90:20:50:100) according to M. Hamberg and B. Samuelsson, J. Biol. Chem. 241, 257 (1966).

Skellysolve-B (SSB) refers to mixed isomeric hexanes.

Silica gel chromatography, as used herein, is understood to include elution, collection of fractions, and combination of those fractions shown by TLC (thin layer chromatography) to contain the pure product (i.e., free of starting material and impurities).

Melting points (MP) are determined on a Fisher-Johns or Thomas-Hoover melting point apparatus.

THF refers to tetrahydrofuran.

Specific Rotations, $[\alpha]$, are determined for solutions of a compound in the specified solvent at ambient temperature with a Perkin-Elmer Model 141 Automatic Polarimeter.

EXAMPLE 1 — Prostacyclin, diacetate, methyl ester (Formula XXIV: $X_2$ is —$COOCH_3$, $R_2$ is hydrogen, g is one, $R_{18}$ is —$OCOCH_3$, $Y_1$ is trans-CH=CH—, $R_5$ of the $M_5$ moiety and $R_3$ and $R_4$ of the $L_1$ moiety are all hydrogen, $R_{12}$ of the $M_5$ moiety is acetyl, and $R_7$ is n-butyl)

A. A solution of 5.0 g of 9-deoxy-6,9α-epoxy-5-iodo-$PGF_1$, methyl ester (R. A. Johnson, et al., J. A. C. S. 99:4182, 1977; a compound according to formula XXII) in 25 ml of pyridine and 10 ml of acetic anhydride is maintained at ambient temperature for 4½ hr. Thereupon ice is added and the formula XXIII diacetate is extracted with ethyl acetate and the organic extracts are then washed with water, cold 3 N aqueous hydrochloric acid, saturated sodium bicarbonate, and brine; dried over sodium sulfate; and evaporated to a residue of crude formula XXIII intermediate under reduced pressure.

B. The residue of part A is then dissolved in a small amount of benzene, which is subsequently removed by evaporation under reduced pressure. Thereafter 50 ml of dry benzene and 10 ml of DBU, 1,5-diazabicyclo[5.4.-0]undec-5-ene is added and the resulting mixture stirred at ambient temperature for 72 hrs. Thereafter water is added and the organic phase is washed successively with additional water and brine; dried with sodium sulfate; and concentrated to a residue, the crude formula XXIV title intermediate. Silica gel TLC $R_f$ in acetone and methylene chloride (16:84) is 0.83. Pure title product is obtained by chromatography on silica gel which is wet-packed in the column in Skellysolve-B containing 5% triethylamine and prewashed with Skellysolve-B containing 0.1% triethylamine. The eluent is 0-50% ethyl acetate in Skellysolve-B containing 1/10% of triethylamine.

The mass spectrum exhibits peaks at 450 (the molecular ion), 390, 363, 359, 300, 299, 259, 247, 245, 243, 143, and 111. Characteristic infrared absorptions are observed at 1735, 1240, and 1695 $cm^{-1}$. NMR absorptions are observed at 5.7-5.5, 5.5, and 4.5, 4.18, 3.67, 2.01, and 1.98δ.

EXAMPLE 2 — 6-oxo-$PGF_1\alpha$, 11,15-diacetate, methyl ester (Formula XXV: $X_2$, $R_2$, g, $R_{18}$, $Y_1$, $M_4$, $L_1$, and $R_7$ are as defined in Example 1)

A solution of 499 mg of the reaction product of Example 1 and 5 ml of tetrahydrofuran is diluted with 1.5 ml of water and stirred for 68 hrs at 25° C. Thereafter a small portion of acetic acid (about 15 drops) is added and stirring is continued for an additional 9 hrs. The formula XXV product is then isolated from the resulting mixture by first adding ethyl acetate, washing with saturated sodium bicarbonate, and brine; drying with sodium sulfate; and concentrating to a residue. This residue is then chromatographed on 50 g of silica gel, eluting with 50-100% ethyl acetate in Skellysolve-B. Fractions containing pure product (405 mg) are combined. Silica gel TLC $R_f$ is 0.38 in ethyl acetate and methylene chloride (16:84). The mass spectrum exhibits peaks at 480, 407, 390, 347, 330, 307, 299, 259, and 247. Characteristic infrared absorptions are observed at 3550, 1740, and 1725 cm$^{-1}$. Characteristic NMR absorptions are observed at 4.5-4.2, and 2.8-2.2δ.

EXAMPLE 3 — 6,7-didehydro-PGI$_1$, diacetate, methyl ester (Formula XXVI: $Z_1$ is —(CH$_2$)$_4$—, and $X_2$, $R_{18}$, $Y_1$, $M_5$, $L_1$, and $R_7$ are as defined in Example 1)

A solution of 1.09 g of the reaction product of Example 2 in 50 ml of benzene is refluxed in the presence of anhydrous magnesium sulfate for about 1.5 hrs. Thereupon there are obtained three products. Title intermediate is represented by the least polar product, exhibiting silica gel TLC $R_f$ of 0.44 in ethyl acetate and hexane (1:3).

A 500 ml sample of the crude product mixture above is chromatographed on silica gel eluting with 10-20% ethyl acetate in Skellysolve-B containing 0.1% triethylamine. Among the least polar fractions there are obtained 163 mg of pure title intermediate. The NMR spectrum is characterized by a close doublet centered at 4.66δ and the infrared spectrum is characterized by an absorption at 1660 cm$^{-1}$, in contrast to the characteristic absorption at 1695 cm$^{-1}$ for prostacyclin.

EXAMPLE 4 — 6,7-didehydro-PGI$_1$, sodium salt (Formula XXVII: $X_4$ is —COO$^-$Na$^+$, $Z_1$ is as defined in Example 3, $R_8$ is hydroxy, and $Y_1$, $M_1$, $L_1$, and $R_7$ are as defined in Example 1)

A solution of 383 mg of the reaction product of Example 3 in 8.5 ml of methanol under a nitrogen atmosphere are treated at 25° C. with a single equivalent (8.8 ml) of 0.1 N sodium methoxide in methanol for 5 hrs. The resulting solution is then concentrated under reduced pressure (removing the methyl acetate by-product), then redissolved in 8.5 ml of methanol and 1.5 ml of water. This solution is then stirred for 12 hrs under a nitrogen atmosphere whereupon 10 ml of water is added and the methanol removed under reduced pressure. The resulting aqueous solution is then freeze-dried, yielding a solid residue of pure title product (0.259 g).

EXAMPLE 5 — 6,7-didehydro-PGI$_1$, tris(hydroxymethyl) aminomethane salt

The title product of Example 4 is acidified with dilute aqueous hydrochloric acid and quickly extracted from the aqueous solution with diethyl ether. The ethereal solution is then combined with stirring with an solution of tris(hydroxymethyl)aminomethane, containing exactly 1 equivalent of this base. The resulting aqueous solution, containing the title salt, is then purified in accordance with the isolation procedure of Example 4, thereby yielding pure title product.

EXAMPLE 6 — 6,7-didehydro-PGI$_1$, methyl ester (Formula XXVIII: $X_1$ is -COOCH$_3$, $Z_1$ is as defined in Example 3, $R_8$ is as defined in Example 4, and $Y_1$, $M_1$, $L_1$, and $R_7$ are as defined in Example 1)

The title product of Example 4 is dissolved in dimethylformamide (DMF) and thereafter there is added one equivalent of methyl iodide. The resulting mixture is then maintained at ambient temperature with stirring for several hours, whereupon silica gel TLC analysis indicates the esterification reaction is complete. Thereafter, the reaction mixture is washed successively with water and brine and concentrated to a residue containing pure title methyl ester.

EXAMPLE 7 — 6,7-didehydro-PGI$_1$, phenyl ester

The title product of Example 4 is dissolved in dimethylformamide and thereafter an equivalent of N-methyl-2-bromopyridium iodide is added with stirring. After several hours, the resulting mixture is combined with one equivalent of phenol in triethylamine and the resulting mixture is maintained at ambient temperature with stirring for several hours. When silica gel TLC analysis indicates the esterification reaction is complete, pure title ester is obtained by the purification techniques described in Example 6.

EXAMPLE 8 — 6,7-didehydro-PGI$_1$, amide

Following the procedure described in R. A. Johnson, et al., J.A.C.S. 99:4182 (1977), but employing PGF$_2$α, amide in place of PGF$_2$α or PGF$_2$α, methyl ester, there is obtained 9-deoxy-6,9α-epoxy-PGF$_1$α, amide. Further, following the procedure of Example 1, there is prepared prostacyclin, diacetate, amide from 9-deoxy-6,9α-epoxy-PGF$_1$, amide.

Following the procedure of Example 2, prostacyclin diacetate amide is transformed to 6-oxo-PGF$_1$α, 11,15-diacetate, amide. Thereafter, following the procedure of Example 3, this 6-oxo-PGF$_1$α-type compound is transformed to 6,7-didehydro-PGI$_1$, diacetate, amide.

Finally, following the procedure of Example 4, 6,7-didehydro-PGI$_1$, diacetate, amide is transformed to the title product.

Following the procedure of the above examples, but employing the appropriate PGF$_2$α, 11-deoxy-PGF$_2$α, or 11-deoxy-11-hydroxymethyl-PGF$_2$α-type starting material, there are prepared
6,7-didehydro-PGI$_1$-type compounds;
11-deoxy-6,7-didehydro-PGI$_1$-type compounds;
11-deoxy-11-hydroxymethyl-6,7-didehydro-PGI$_1$-type compounds; as amides, esters, or pharmacologically acceptable salts which exhibit the following side chain substituents:
15-Methyl;
16-Methyl;
15,16-Dimethyl-;
16,16-Dimethyl-;
16-Fluoro-;
15-Methyl-16-fluoro-;
16,16-Difluoro-;
15-Methyl-16,16-difluoro-;
17-Phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
15-Methyl-17-phenyl-18,19,20-trinor-;
16-Methyl-17-phenyl-18,19,20-trinor-;
16,16-Dimethyl-17-phenyl-18,19,20-trinor-;

16-Fluoro-17-phenyl-18,19,20-trinor-;
16,16-Difluoro-17-phenyl-18,19,20-trinor-;
16-Phenyl-17,18,19,20-tetranor-;
15-Methyl-16-phenyl-17,18,19,20-tetranor-;
16-(m-trifluoromethylphenyl)-17,18,19,20-tetranor-;
16-(m-chlorophenyl)-17,18,19,20-tetranor-;
16-(p-fluorophenyl)-17,18,19,20-tetranor-;
16-Phenyl-18,19,20-trinor-;
15-Methyl-16-phenyl-18,19,20-trinor-;
16-Methyl-16-phenyl-18,19,20-trinor-;
15,16-Dimethyl-16-phenyl-18,19,20-trinor-;
16-Phenoxy-17,18,19,20-tetranor-;
15-Methyl-16-phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
16-Phenoxy-18,19,20-trinor-;
15-Methyl-16-phenoxy-18,19,20-trinor-;
16-Methyl-16-phenoxy-18,19,20-trinor-;
15,16-Dimethyl-16-phenoxy-18,19,20-trinor-;
13,14-Didehydro-;
16-Methyl-13,14-didehydro-;
16,16-Dimethyl-13,14-didehydro-;
16-Fluoro-13,14-didehydro-;
16,16-Difluoro-13,14-didehydro-;
17-Phenyl-18,19,20-trinor-13,14-didehydro-;
17-(m-trifluoromethylphenyl)-18,19,20-trinor-13,14-didehydro-;
17-(m-chlorophenyl)-18,19,20-trinor-13,14-didehydro-;
17-(p-fluorophenyl)-18,19,20-trinor-13,14-didehydro-;
16-Methyl-17-phenyl-18,19,20-trinor-13,14-didehydro-;
16,16-Dimethyl-17-phenyl-18,19,20-trinor-13,14-didehydro-;
16-Fluoro-17-phenyl-18,19,20-trinor-13,14-didehydro-;
16,16-Difluoro-17-phenyl-18,19,20-trinor-13,14-didehydro-;
16-Phenyl-17,18,19,20-tetranor-13,14-didehydro-;
16-(m-trifluoromethylphenyl)-17,18,19,20-tetranor-13,14-didehydro-;
16-(m-chlorophenyl)-17,18,19,20-tetranor-13,14-didehydro-;
16-Phenyl-18,19,20-trinor-13,14-didehydro-;
16-Methyl-16-phenyl-18,19,20-trinor-13,14-didehydro-;
16-Phenoxy-17,18,19,20-tetranor-13,14-didehydro-;
16-(m-trifluoromethylphenoxy)-17,18,19,20-tetranor-13,14-didehydro-;
16-(m-chlorophenoxy)-17,18,19,20-tetranor-13,14-didehydro-;
16-Phenoxy-18,19,20-trinor-13,14-didehydro-;
16-Methyl-16-phenoxy-18,19,20-trinor-13,14-didehydro-;
13,14-Dihydro-;
16-Methyl-13,14-dihydro-;
16,16-Dimethyl-13,14-dihydro-;
16-Fluoro-13,14-dihydro-;
16,16-Difluoro-13,14-dihydro-;
17-Phenyl-18,19,20-trinor-13,14-dihydro-;
17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
16-Methyl-17-phenyl-18,19,20-trinor-13,14-dihydro-;
16,16-Dimethyl-17-phenyl-18,19,20-trinor-13,14-dihydro-;
16-Fluoro-17-phenyl-18,19,20-trinor-13,14-dihydro-;
16,16-Difluoro-17-phenyl-18,19,20-trinor-13,14-dihydro-;
16-Phenyl-17,18,19,20-tetranor-13,14-dihydro-;
16-(m-trifluoromethylphenyl)-17,18,19,20-tetranor-13,14-dihydro-;
16-(m-chlorophenyl)-17,18,19,20-tetranor-13,14-dihydro-;
16-(p-fluorophenyl)-17,18,19,20-tetranor-13,14-dihydro-;
16-Phenyl-18,19,20-trinor-13,14-dihydro-;
16-Methyl-16-phenyl-18,19,20-trinor-13,14-dihydro-;
16-Phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-Phenoxy-18,19,20-trinor-13,14-dihydro-;
16-Methyl-16-phenoxy-18,19,20-trinor-13,14-dihydro-;
13-cis-;
16-Methyl-13-cis-;
16,16-Dimethyl-13-cis-;
16-Fluoro-b 13-cis-;
16,16-Difluoro-13-cis-;
17-Phenyl-18,19,20-trinor-13-cis-;
17-(m-trifluoromethylphenyl)-18,19,20-trinor-13-cis-;
17-(m-chlorophenyl)-18,19,20-trinor-13-cis-;
17-(p-fluorophenyl)-18,19,20-trinor-13-cis-;
16-Methyl-17-phenyl-18,19,20-trinor-13-cis-;
16,16-Dimethyl-17-phenyl-18,19,20-trinor-13-cis-;
16-Fluoro-17-phenyl-18,19,20-trinor-13-cis-;
16,16-Difluoro-17-phenyl-18,19,20-trinor-13-cis-;
16Phenyl-17,18,19,20-tetranor-13-cis-;
16-(m-trifluoromethylphenyl)-17,18,19,20-tetranor-13-cis-;
16-(m-chlorophenyl)-17,18,19,20-tetranor-13-cis-;
16-(p-fluorophenyl)-17,18,19,20-tetranor-13-cis-;
16-Phenyl-18,19,20-trinor-13-cis-;
16-Methyl-16-phenyl-18,19,20-trinor-13-cis-;
16-Phenoxy-17,18,19,20-tetranor-13-cis-;
16-(m-trifluoromethylphenoxy)-17,18,19,20-tetranor-13-cis-;
16-(m-chlorophenoxy)-17,18,19,20-tetranor-13-cis-;
16-(p-fluorophenoxy)-17,18,19,20-tetranor-13-cis-;
16-Phenoxy-18,19,20-trinor-13-cis-;
16-Methyl-16-phenoxy-18,19,20-trinor-13-cis-;
2,2-Difluoro-;
2,2-Difluoro-15-methyl-;
2,2-Difluoro-16-methyl-;
2,2-Difluoro-16,16-dimethyl-;
2,2-Difluoro-16-fluoro-;
2,2-Difluoro-16,16-difluoro-;
2,2-Difluoro-17-phenyl-18,19,20-trinor-;
2,2-Difluoro-17-(m-trifluoromethylphenyl)-18,19,20-trinor-;
2,2-Difluoro-17-(m-chlorophenyl)-18,19,20-trinor-;
2,2-Difluoro-17-(p-fluorophenyl)-18,19,20-trinor-;
2,2-Difluoro-16-methyl-17-phenyl-18,19,20-trinor-;
2,2-Difluoro-16,16-dimethyl-17-phenyl-18,19,20-trinor-;
2,2-Difluoro-16-fluoro-17-phenyl-18,19,20-trinor-;
2,2-Difluoro-16,16-difluoro-17-phenyl-18,19,20-trinor-;
2,2-Difluoro-16-phenyl-17,18,19,20-tetranor-;
2,2-Difluoro-16-(m-trifluoromethylphenyl)-17,18,19,20-tetranor-;
2,2-Difluoro-16-(m-chlorophenyl)-17,18,19,20-tetranor-;
2,2-Difluoro-16-(p-fluorophenyl)-17,18,19,20-tetranor-;
2,2-Difluoro-16-phenyl-18,19,20-trinor-;
2,2-Difluoro-16-methyl-16-phenyl-18,19,20-trinor-;
2,2-Difluoro-16-phenoxy-17,18,19,20-tetranor-;

2,2-Difluoro-16-(m-trifluoromethylphenoxy)-17,18,19,20-tetranor-;
2,2-Difluoro-16-(m-chlorophenoxy)-17,18,19,20-tetranor-;
2,2-Difluoro-16-(p-fluorophenoxy)-17,18,19,20-tetranor-;
2,2-Difluoro-16-phenoxy-18,19,20-trinor-;
2,2-Difluoro-16-methyl-16-phenoxy-18,19,20-trinor-;
2,2-Difluoro-16-methyl-13,14-didehydro-;
2,2-Difluoro-16,16-dimethyl-13,14-didehydro-;
2,2-Difluoro-16-fluoro-13,14-didehydro-;
2,2-Difluoro-16,16-difluoro-13,14-didehydro-;
2,2-Difluoro-17-phenyl-18,19,20-trinor-13,14-didehydro-;
2,2-Difluoro-17-(m-trifluoromethylphenyl)-18,19,20-trinor-13,14-didehydro-;
2,2-Difluoro-17-(m-chlorophenyl)-18,19,20-trinor-13,14-didehydro-;
2,2-Difluoro-17-(p-fluorophenyl)-18,19,20-trinor-13,14-didehydro-;
2,2-Difluoro-16-methyl-17-phenyl-18,19,20-trinor-13,14-didehydro-;
2,2-Difluoro-16,16-dimethyl-17-phenyl-18,19,20-trinor-13,14-didehydro-;
2,2,16-Trifluoro-17-phenyl-18,19,20-trinor-13,14-didehydro-;
2,2,16,16-Tetrafluoro-17-phenyl-18,19,20-trinor-13,14-didehydro-;
2,2-Difluoro-16-phenyl-17,18,19,20-tetranor-13,14-didehydro-;
2,2-Difluoro-16-(m-trifluoromethylphenyl)-17,18,19,20-tetranor-13,14-didehydro-;
2,2-Difluoro-16-(m-chlorophenyl)-17,18,19,20-tetranor-13,14-didehydro-;
2,2-Difluoro-16-phenyl-18,19,20-trinor-13,14-didehydro-;
2,2-Difluoro-16-methyl-16-phenyl-18,19,20-trinor-13,14-didehydro-;
2,2-Difluoro-16-phenoxy-17,18,19,20-tetranor-13,14-didehydro-;
2,2-Difluoro-16-(m-trifluoromethylphenoxy)-17,18,19,20-tetranor-13,14-didehydro-;
2,2-Difluoro-16-(m-chlorophenoxy)-17,18,19,20-tetranor-13,14-didehydro-;
2,2-Difluoro-16-phenoxy-18,19,20-trinor-13,14-didehydro-;
2,2-Difluoro-16-methyl-16-phenoxy-18,19,20-trinor-13,14-didehydro-;
2,2-Difluoro-13,14-dihydro-;
2,2-Difluoro-16-methyl-13,14-dihydro-;
2,2-Difluoro-16,16-dimethyl-13,14-dihydro-;
2,2,16-Trifluoro-13,14-dihydro-;
2,2,16,16-Tetrafluoro-13,14-dihydro-;
2,2-Difluoro-17-phenyl-18,19,20-trinor-13,14-dihydro-;
2,2-Difluoro-17-(m-trifluoromethylphenyl)-18,19,20-trinor-13,14-dihydro-;
2,2-Difluoro-17-(m-chlorophenyl)-18,19,20-trinor-13,14-dihydro-;
2,2-Difluoro-17-(p-fluorophenyl)-18,19,20-trinor-13,14-dihydro-;
2,2-Difluoro-16-methyl-17-phenyl-18,19,20-trinor-13,14-dihydro-;
2,2-Difluoro-16,16-dimethyl-17-phenyl-18,19,20-trinor-13,14-dihydro-;
2,2,16-Trifluoro-17-phenyl-18,19,20-trinor-13,14-dihydro-;
2,2,16,16-Tetrafluoro-17-phenyl-18,19,20-trinor-13,14-dihydro-;
2,2-Difluoro-16-phenyl-17,18,19,20-tetranor-13,14-dihydro-;
2,2-Difluoro-16-(m-trifluoromethylphenyl)-17,18,19,20-tetranor-13,14-dihydro-;
2,2-Difluoro-16-(m-chlorophenyl)-17,18,19,20-tetranor-13,14-dihydro-;
2,2-Difluoro-16-(p-fluorophenyl)-17,18,19,20-tetranor-13,14-dihydro-;
2,2-Difluoro-16-phenyl-16-phenyl-18,19,20-trinor-13,14-dihydro-;
2,2-Difluoro-16-methyl-16-phenyl-18,19,20-trinor-13,14-dihydro-;
2,2-Difluoro-16-phenoxy-17,18,19,20-tetranor-13,14-dihydro-;
2,2-Difluoro-16-(m-trifluoromethylphenoxy)-17,18,19,20-tetranor-13,14-dihydro-;
2,2-Difluoro-16-(m-chlorophenoxy)-17,18,19,20-tetranor-13,14-dihydro-;
2,2-Difluoro-16-(p-fluorophenoxy)-17,18,19,20-tetranor-13,14-dihydro-;
2,2-Difluoro-16-methyl-16-phenoxy-18,19,20-trinor-13,14-dihydro-;
2,2-Difluoro-13-cis-;
2,2-Difluoro-16-methyl-13-cis-;
2,2-Difluoro-16,16-dimethyl-13-cis-;
2,2,16-Trifluoro-13-cis-;
2,2,16,16-Tetrafluoro-13-cis-;
2,2-Difluoro-17-phenyl-18,19,20-trinor-13-cis-;
2,2-Difluoro-17-(m-trifluomethylphenyl)-18,19,20-trinor-13-cis-;
2,2-Difluoro-17-(m-chlorophenyl)-18,19,20-trinor-13-cis-;
2,2-Difluoro-17-(m-fluorophenyl)-18,19,20-trinor-13-cis-;
2,2-Difluoro-16-methyl-17-phenyl-18,19,20-trinor-13-cis-;
2,2-Difluoro-16,16-dimethyl-17-phenyl-18,19,20-trinor-13-cis-;
2,2,16-Trifluoro-17-phenyl-18,19,20-trinor-13-cis-;
2,2,16,16-Tetrafluoro-17-phenyl-18,19,20-trinor-13-cis-;
2,2-Difluoro-16-phenyl-17,18,19,20-tetranor-13-cis-;
2,2-Difluoro-16-(m-trifluoromethylphenyl)-17,18,19,20-tetranor-13-cis-;
2,2-Difluoro-16-(m-chlorophenyl)-17,18,19,20-tetranor-13-cis-;
2,2-Difluoro-(p-fluorophenyl)-17,18,19,20-tetranor-13-cis-;
2,2-Difluoro-16-phenyl-18,19,20-trinor-13-cis-;
2,2-Difluoro-16-methyl-16-phenyl-18,19,20-trinor-13-cis-;
2,2-Difluoro-16-phenoxy-17,18,19,20-tetranor-13-cis-;
2,2-Difluoro-16-(m-trifluoromethylphenoxy)-17,18,19,20-tetranor-13-cis-;
2,2-Difluoro-16-(m-chlorophenoxy)-17,18,19,20-tetranor-13-cis-;
2,2-Difluoro-16-(p-fluorophenoxy)-17,18,19,20-tetranor-13-cis-;
2,2-Difluoro-16-phenoxy-18,19,20-trinor-13-cis-;
2,2-Difluoro-16-methyl-16-phenoxy-18,19,20-trinor-13-cis-, Further, employing the corresponding 2-decarboxy-2-hydroxymethyl- or 2-aminomethyl starting materials, there are prepared corresponding products to each of the carboxylate prostacyclin analogs described above.

I claim:

1. A prostacyclin intermediate of the formula

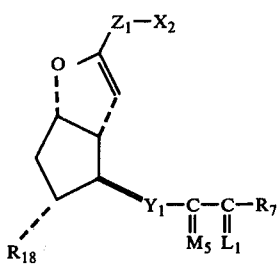

wherein $Z_1$ is
(1) —$(CH_2)_g$—$(CH_2)_2$—$CH_2$—, or
(2) —$(CH_2)_g$—$(CH_2)_2$—$CF_2$—,
wherein g is the integer one, 2, or 3;
  wherein $R_{18}$ is hydrogen; alkanoyloxy of two to 8 carbon atoms, inclusive, or alkanoyloxymethyl of two to 8 carbon atoms, inclusive;
wherein $Y_1$ is
(1) trans—CH=CH—,
(2) cis—CH=CH—,
(3) —$CH_2CH_2$—, or
(4) —C≡C—;
wherein $M_5$ is

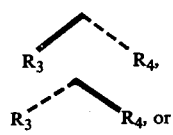

wherein $R_5$ is hydrogen or methyl and $R_{12}$ is alkanoyl of two to 8 carbon atoms, inclusive;
wherein $L_1$ is

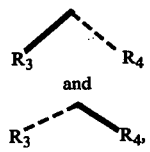

a mixture of

wherein $R_3$ and $R_4$ are hydrogen, methyl, or fluoro, being the same or different, with the proviso that one of $R_3$ and $R_4$ is fluoro only when the other is hydrogen or fluoro;
  wherein $X_2$ is
  (1) —$COOR_2$ wherein $R_2$ is alkyl of one to 12 carbon atoms, inclusive; cycloalkyl of 3 to 10 carbon atoms, inclusive; aralkyl of 7 to 12 carbon atoms, inclusive; phenyl; phenyl substituted with one, two or three chloro or alkyl of one to 3 carbon atoms; phenyl substituted in the para position by

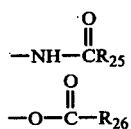

(a)

(b)

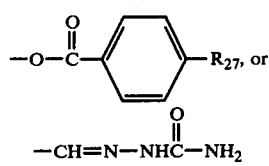

(c)

(d)

wherein $R_{25}$ is methyl, phenyl, acetamidophenyl, benzamidophenyl, or —$NH_2$; $R_{26}$ is methyl, phenyl, —$NH_2$, or methoxy; and $R_{27}$ is hydrogen or acetamido; phenacyl, i.e.,

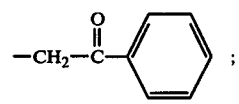

or phenacyl substituted in the para position by chloro, bromo, phenyl, or benzamido;
  (2)

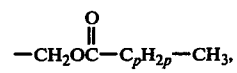

wherein p is zero, one, 2, 3, 4, 5, or 6;
  (3) —$CH_2NL_2L_3$ wherein $L_2$ and $L_3$ are hydrogen or alkyl of one to 4 carbon atoms, inclusive; or
  (4) —$COL_4$, wherein $L_4$ is
  (a) amino of the formula -$NR_{21}R_{22}$; wherein $R_{21}$ and $R_{22}$ are
  (i) hydrogen;
  (ii) alkyl of one to 12 carbon atoms, inclusive;
  (iii) cycloalkyl of 3 to 10 carbon atoms, inclusive;
  (iv) aralkyl of 7 to 12 carbon atoms, inclusive;
  (v) phenyl;
  (vi) phenyl substituted with one, 2, or 3 chloro, alkyl of one to 3 carbon atoms, inclusive, hydroxy, carboxy, alkoxycarbonyl of one to 4 carbon atoms, inclusive, or nitro;
  (vii) carboxyalkyl of one to 4 carbon atoms, inclusive;
  (viii) carbamoylalkyl of one to 4 carbon atoms, inclusive;
  (ix) cyanoalkyl of one to 4 carbon atoms, inclusive;
  (x) acetylalkyl of one to 4 carbon atoms, inclusive;
  (xi) benzoylalkyl of one to 4 carbon atoms, inclusive;
  (xii) benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro;
  (xiii) pyridyl;
  (xiv) pyridyl substituted by one, 2, or 3 chloro, alkyl of one to 3 carbon atoms, inclusive, or alkoxy of one to 3 carbon atoms, inclusive;
  (xv) pyridylalkyl of one to 4 carbon atoms, inclusive;
  (xvi) pyridylalkyl substituted by one, 2, or 3 chloro, alkyl of one to 3 carbon atoms, inclusive, hydroxy, or alkoxy of one to 3 carbon atoms, inclusive;
  (xvii) hydroxyalkyl of one to 4 carbon atoms, inclusive;
  (xviii) dihydroxyalkyl of one to 4 carbon atoms, or (xix) trihydroxyalkyl of one to 4 carbon atoms;
with the further proviso that not more than one of $R_{21}$ and $R_{22}$ is other than hydrogen or alkyl;

(b) cycloamino selected from the group consisting of

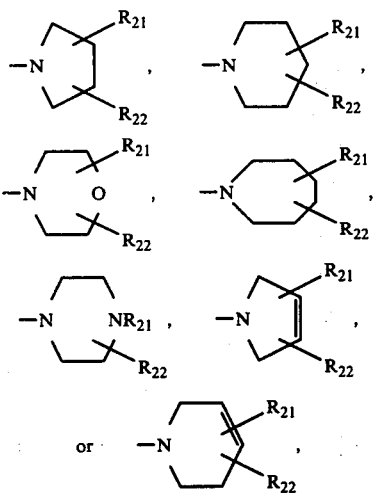

wherein $R_{21}$ and $R_{22}$ are as defined above;

(c) carbonylamino of the formula $-NR_{23}COR_{21}$, wherein $R_{23}$ is hydrogen or alkyl of one to 4 carbon atoms and $R_{21}$ is as defined above;

(d) sulphonylamino of the formula $-NR_{23}SO_2R_{21}$, wherein $R_{21}$ and $R_{22}$ are as defined above; or (e) hydrazino of the formula $-NR_{23}R_{24}$, wherein $R_{23}$ is as defined above and $R_{24}$ is amino of the formula $-NR_{21}R_{22}$, as defined above, or cycloamino, as defined above;

wherein $R_7$ is (1) $-(CH_2)_m-CH_3$,

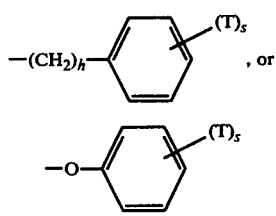

wherein m is the integer one to 5, inclusive, h is the integer zero to 3, inclusive; s is the integer zero, one, 2, or 3, and T is chloro, fluoro, trifluoromethyl, alkyl of one to 3 carbon atoms, inclusive, or alkoxy of one to 3 carbon atoms, inclusive, with the proviso that not more than two T's are other than alkyl.

2. 6,7-Didehydro-PGI$_1$, methyl ester, diacetate, a prostacyclin intermediate according to claim 1.

3. A prostacyclin analog of the formula

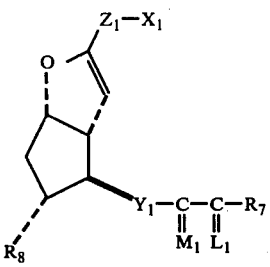

wherein $Z_1$ is (1) $-(CH_2)_g-(CH_2)_2-CH_2-$, or
(2) $-(CH_2)_g-(CH_2)_2-CF_2-$, wherein g is the integer one, 2, or 3;

wherein $Y_1$ is (1) trans$-CH=CH-$,
(2) cis$-CH=CH-$,
(3) $-CH_2CH_2-$, or
(4) $-C\equiv C-$;

wherein $M_1$ is

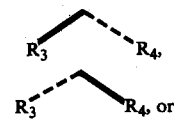

wherein $R_5$ is hydrogen or alkyl with one to 4 carbon atoms, inclusive, wherein $L_1$ is

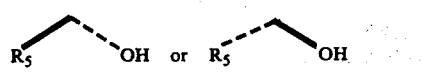

a mixture of

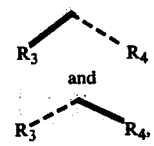

wherein $R_3$ and $R_4$ are hydrogen, methyl, or fluoro, being the same or different, with the proviso that one of $R_3$ and $R_4$ is fluoro only when the other is hydrogen or fluoro;

wherein $X_1$ is (1) $-COOR_{10}$, wherein $R_{10}$ is hydrogen, alkyl of one to 12 carbon atoms, inclusive; cycloalkyl of 3 to 10 carbon atoms, inclusive; aralkyl of 7 to 12 carbon atoms, inclusive; phenyl; phenyl substituted with one, two or three chloro or alkyl of one to 3 carbon atoms; phenyl substituted in the para position by

 (a)

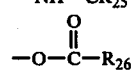 (b)

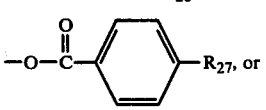 (c)

-continued

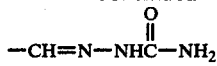 (d)

wherein R$_{25}$ is methyl, phenyl, acetamidophenyl, benzamidophenyl, or —NH$_2$; R$_{26}$ is methyl, phenyl, —NH$_2$, or methoxy; and R$_{27}$ is hydrogen or acetamido; phenacyl, i.e.,

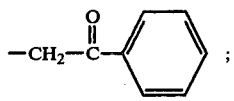

phenacyl substituted in the para position by chloro, bromo, phenyl, or benzamido; or a pharmacologically acceptable cation;

(2) —CH$_2$OH;
(3) —CH$_2$NL$_2$L$_3$ wherein L$_2$ and L$_3$ are hydrogen or alkyl of one to 4 carbon atoms, inclusive; or
(4) —COL$_4$, wherein L$_4$ is
  (a) amino of the formula —NR$_{21}$R$_{22}$; wherein R$_{21}$ and R$_{22}$ are
    (i) hydrogen;
    (ii) alkyl of one to 12 carbon atoms, inclusive;
    (iii) cycloalkyl of 3 to 10 carbon atoms, inclusive;
    (iv) aralkyl of 7 to 12 carbon atoms, inclusive;
    (v) phenyl;
    (vi) phenyl substituted with one, 2, or 3 chloro, alkyl of one to 3 carbon atoms, inclusive, hydroxy, carboxy, alkoxycarbonyl of one to 4 carbon atoms, inclusive, or nitro;
    (vii) carboxyalkyl of one to 4 carbon atoms, inclusive;
    (viii) carbamoylalkyl of one to 4 carbon atoms, inclusive;
    (ix) cyanoalkyl of one to 4 carbon atoms, inclusive;
    (x) acetylalkyl of one to 4 carbon atoms, inclusive;
    (xi) benzoylalkyl of one to 4 carbon atoms, inclusive;
    (xii) benzoylalkyl substituted by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro;
    (xiii) pyridyl;
    (xiv) pyridyl substituted by one, 2, or 3 chloro, alkyl of one to 3 carbon atoms, inclusive, or alkoxy of one to 3 carbon atoms, inclusive;
    (xv) pyridylalkyl of one to 4 carbon atoms, inclusive;
    (xvi) pyridylalkyl substituted by one, 2, or 3 chloro, alkyl of one to 3 carbon atoms, inclusive, hydroxy, or alkoxy of one to 3 carbon atoms, inclusive;
    (xvii) hydroxyalkyl of one to 4 carbon atoms, inclusive;
    (xviii) dihydroxyalkyl of one to 4 carbon atoms, or
    (xix) trihydroxyalkyl of one to 4 carbon atoms; with the further proviso that not more than one of R$_{21}$ and R$_{22}$ is other than hydrogen or alkyl;
  (b) cycloamino selected from the group consisting of

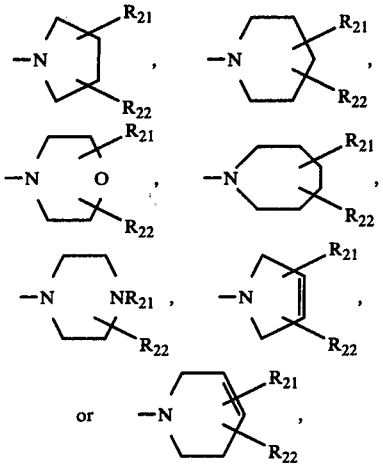

wherein R$_{21}$ and R$_{22}$ are as defined above;
  (c) carbonylamino of the formula —NR$_{23}$COR$_{21}$, wherein R$_{23}$ is hydrogen or alkyl of one to 4 carbon atoms and R$_{21}$ is as defined above;
  (d) sulphonylamino of the formula —NR$_{23}$SO$_2$R$_{21}$, wherein R$_{21}$ and R$_{22}$ are as defined above; or
  (e) hydrazino of the formula —NR$_{23}$R$_{24}$, wherein R$_{23}$ is as defined above and R$_{24}$ is amino of the formula —NR$_{21}$R$_{22}$, as defined above, or cycloamino, as defined above;
wherein R$_7$ is
(1) —(CH$_2$)$_m$—CH$_3$,

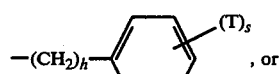 (2)

, or

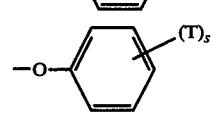 (3)

wherein m is the integer one to 5, inclusive, h is the integer zero to 3, inclusive; s is the integer zero, one, 2, or 3, and T is chloro, fluoro, trifluoromethyl, alkyl of one to 3 carbon atoms, inclusive, or alkoxy of one to 3 carbon atoms, inclusive, with the proviso that not more than two T's are other than alkyl, wherein M$_1$ is

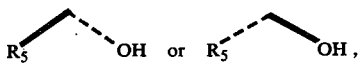

wherein R$_5$ is hydrogen or methyl; and
wherein R$_8$ is hydrogen, hydroxy, or hydroxymethyl.

4. A prostacyclin analog according to claim 3, wherein R$_8$ is hydroxymethyl.

5. 11-Deoxy-11α-hydroxymethyl-6,7-didehydro-PGI$_1$, a prostacyclin analog according to claim 4.

6. A prostacyclin analog according to claim 3, wherein R$_8$ is hydrogen.

7. 11-Deoxy-6,7-didehydro-PGI$_1$, a prostacyclin analog according to claim 6.

8. A prostacyclin analog according to claim 3, wherein R$_8$ is hydroxy.

9. A prostacyclin analog according to claim 8, wherein Y$_1$ is —C≡C—.

10. 6,7,13,14-Tetradehydro-PGI$_1$, methyl ester, a prostacyclin analog according to claim 9.

11. 15-Methyl-6,7,13,14-tetradehydro-PGI$_1$, methyl ester, a prostacyclin analog according to claim 9.

12. 16,16-Dimethyl-6,7,13,14-tetradehydro-PGI$_1$, methyl ester, a prostacyclin analog according to claim 9.

13. 2,2-Difluoro-15-methyl-6,7,13,14-tetradehydro-PGI$_1$, methyl ester, a prostacyclin analog according to claim 9.

14. A prostacyclin analog according to claim 8, wherein Y$_1$ is cis-CH=CH-.

15. cis-13-6,7-Didehydro-PGI$_1$, methyl ester, a prostacylcin analog according to claim 14.

16. A prostacyclin analog according to claim 8, wherein Y$_1$ is -CH$_2$CH$_2$-.

17. 13,14-Dihydro-6,7-didehydro-PGI$_1$, methyl ester, a prostacyclin analog according to claim 16.

18. 13,14-Dihydro-15-methyl-6,7-didehydro-PGI$_1$, methyl ester, a prostacyclin analog according to claim 16.

19. 13,14-Dihydro-16,16-dimethyl-6,7-didehydro-PGI$_1$, methyl ester, a prostacyclin analog according to claim 16.

20. 13,14-Dihydro-2,2-difluoro-15-methyl-6,7-didehydro-PGI$_1$, methyl ester, a prostacyclin analog according to claim 16.

21. 13,14-Dihydro-2,2,16,16-tetrafluoro-6,7-didehydro-PGI$_1$, methyl ester, a prostacyclin analog according to claim 16.

22. A prostacyclin analog according to claim 8, wherein Y$_1$ is trans-CH=CH-.

23. A prostacyclin analog according to claim 22, wherein Z$_1$ is —(CH$_2$)$_g$-(CH$_2$)$_2$-CF$_2$.

24. 2,2-Difluoro-15-methyl-6,7-didehydro-PGI$_1$, methyl ester, a prostacyclin analog according to claim 23.

25. 2,2-Difluoro-16,16-dimethyl-6,7-didehydro-PGI$_1$, methyl ester, a prostacyclin analog according to claim 23.

26. 2,2,16,16-Tetrafluoro-6,7-didehydro-PGI$_1$, methyl ester, a prostacyclin analog according to claim 23.

27. A prostacyclin analog according to claim 22, wherein Z$_1$ is -(CH$_2$)$_g$-(CH$_2$)$_2$-CH$_2$-.

28. A prostacyclin analog according to claim 27, wherein g is one.

29. A prostacyclin analog according to claim 28, wherein R$_7$ is

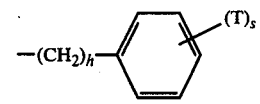

30. 17-Phenyl-18,19,20-trinor-6,7-didehydro-PGI$_1$, methyl ester, a prostacyclin analog according to claim 29.

31. A prostacyclin analog according to claim 28, wherein R$_7$ is

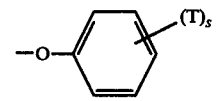

32. 16-Phenoxy-17,18,19,20-tetranor-6,7-didehydro-PGI$_1$, methyl ester, a prostacyclin analog according to claim 31.

33. A prostacyclin analog according to claim 28, wherein R$_7$ is -(CH$_2$)$_m$-CH$_3$.

34. A prostacyclin analog according to claim 33, wherein m is 3.

35. A prostacyclin analog according to claim 34, wherein X$_1$ is -COL$_4$.

36. 6,7-Didehydro-PGI$_1$, amide, a prostacyclin analog according to claim 35.

37. A prostacyclin analog according to claim 35, wherein X$_1$ is -CH$_2$OH.

38. 2-Decarboxy-2-hydroxymethyl-6,7-didehydro-PGI$_1$, a prostacyclin analog according to claim 37.

39. A prostacyclin analog according to claim 34, wherein X$_1$ is -COOR$_{10}$.

40. A prostacyclin analog according to claim 39, wherein R$_5$ is methyl.

41. 15-Methyl-6,7-didehydro-PGI$_1$, methyl ester, a prostacyclin analog according to claim 40.

42. A prostacyclin analog according to claim 39, wherein R$_5$ is hydrogen.

43. A prostacyclin analog according to claim 42, wherein at least one of R$_3$ and R$_4$ is fluoro.

44. 16,16-Difluoro-6,7-didehydro-PGI$_1$, methyl ester, a prostacyclin analog according to claim 43.

45. A prostacyclin analog according to claim 42, wherein at least one of R$_3$ and R$_4$ is methyl.

46. 16,16-Dimethyl-6,7-didehydro-PGI$_1$, methyl ester, a prostacyclin analog according to claim 45.

47. A prostacyclin analog according to claim 42, wherein R$_3$ and R$_4$ are both hydrogen.

48. 6,7-Didehydro-PGI$_1$, methyl ester, a prostacyclin analog according to claim 47.

49. 6,7-Didehydro-PGI$_1$, tris(hydroxymethyl)aminomethane salt, a prostacyclin analog according to claim 47.

50. 6,7-Didehydro-PGI$_1$, adamantanamine salt, a prostacyclin analog according to claim 47.

51. 6,7-Didehydro-PGI$_1$, sodium salt, a prostacyclin analog according to claim 47.

* * * * *

UNITED STATES PATENT OFFICE
CERTIFICATE OF CORRECTION

Patent No. 4,128,713                    Dated December 5, 1978

Inventor(s) William P. Schneider

It is certified that error appears in the above-identified patent and that said Letters Patent are hereby corrected as shown below:

Column 3, lines 22-30, that portion of the formula reading should read:

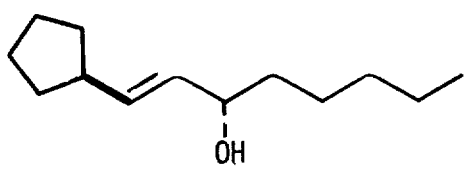

Column 3, lines 41-45, that portion of the formula reading

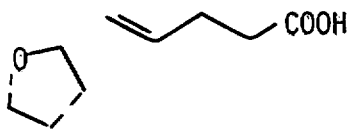

should read:

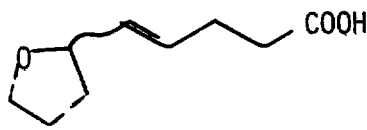

Column 5, line 30, "ot nitro;" should read -- or nitro; --

UNITED STATES PATENT OFFICE
CERTIFICATE OF CORRECTION

Patent No. 4,128,713     Dated December 5, 1978

Inventor(s) William P. Schneider

It is certified that error appears in the above-identified patent and that said Letters Patent are hereby corrected as shown below:

Column 9, line 62, "2,6-, 3,4-, or 3,5-(" should read -- 2,6-, 3,4-, or 3,5-) --; line 63, "(3-, or 4-(" should read -- (3-, or 4-) --; line 64, "(o-, m-, or p-" should read -- (o-, m-, or p-) --.

Column 12, line 6, "1-hdroxyethylamide" should read -- 1-hydroxyethylamide --;

Column 37, line 42, "-$(CH_2)_g$-$(CH_2)_2$-$CF_2$." should read -- -$(CH_2)_g$-$(CH_2)_2$-$CF_2$-. --.

Signed and Sealed this

Twenty-ninth Day of May 1979

[SEAL]

Attest:

RUTH C. MASON
Attesting Officer

DONALD W. BANNER
Commissioner of Patents and Trademarks